US012698935B2

(12) United States Patent
Pettersson et al.

(10) Patent No.: US 12,698,935 B2
(45) Date of Patent: Aug. 4, 2026

(54) ELECTROSTATIC SPRAY DRYING OF MICROORGANISMS

(71) Applicant: Chr. Hansen A/S, Hoersholm (DK)

(72) Inventors: Jimi Kjaersgaard Pettersson, Hoersholm (DK); Wendy Ossieur, Hoersholm (DK); Michelle Milling Madsen, Hoersholm (DK); Kim Nielsen, Hoersholm (DK)

(73) Assignee: Chr. Hansen A/S, Hoersholm (DK)

( * ) Notice: Subject to any disclaimer, the term of this patent is extended or adjusted under 35 U.S.C. 154(b) by 874 days.

(21) Appl. No.: 17/795,211

(22) PCT Filed: Jan. 29, 2021

(86) PCT No.: PCT/EP2021/052136
§ 371 (c)(1),
(2) Date: Jul. 25, 2022

(87) PCT Pub. No.: WO2021/152111
PCT Pub. Date: Aug. 5, 2021

(65) Prior Publication Data
US 2023/0341182 A1 Oct. 26, 2023

(30) Foreign Application Priority Data
Jan. 31, 2020 (EP) .................................... 20154883

(51) Int. Cl.
*F26B 3/12* (2006.01)
*B01D 1/16* (2006.01)
(Continued)

(52) U.S. Cl.
CPC ............... *F26B 3/12* (2013.01); *C12M 35/02* (2013.01); *C12M 47/14* (2013.01); *C12N 13/00* (2013.01)

(58) Field of Classification Search
CPC .... F26B 3/12; F26B 5/06; F26B 5/065; F01D 1/16; F05B 17/00
(Continued)

(56) References Cited

U.S. PATENT DOCUMENTS 8,939,388 B1 1/2015 Beetz et al.
9,332,776 B1 5/2016 Beetz et al.
(Continued)

FOREIGN PATENT DOCUMENTS

CN 107427806 A 12/2017
CN 107960055 A 4/2018
(Continued)

OTHER PUBLICATIONS

English translation of DE102005020561 by PE2E Jul. 18, 2025.*
(Continued)

*Primary Examiner* — Deming Wan
(74) *Attorney, Agent, or Firm* — Eric J. Fechter

(57) ABSTRACT

The present disclosure relates to a process for electrostatic spray drying of a living microorganism, the process comprising the following steps: a. Providing a suspension, comprising a number of components, including a microorganism, a solvent and an additive; b. Applying an electrostatic charge to said suspension; c. Forming droplets of said suspension; d. Drying said droplets, thereby forming dried particles; and e. (Optionally) collecting the dried particles.

21 Claims, 8 Drawing Sheets

(51) Int. Cl.

| | |
|---|---|
| *B05B 17/00* | (2006.01) |
| *C12M 1/00* | (2006.01) |
| *C12M 1/42* | (2006.01) |
| *C12N 13/00* | (2006.01) |
| *F26B 5/06* | (2006.01) |

(58) Field of Classification Search
USPC .......................................... 34/360, 372, 373
See application file for complete search history.

(56) References Cited

U.S. PATENT DOCUMENTS

| | | | |
|---|---|---|---|
| 9,551,527 B2 | 1/2017 | Beetz et al. | |
| 9,993,787 B1 | 6/2018 | Beetz et al. | |
| 10,864,457 B2 * | 12/2020 | Madsen .................. | B05B 17/00 |
| 2006/0071357 A1 | 4/2006 | Pilon et al. | |
| 2018/0104618 A1 | 4/2018 | Fonseca et al. | |

FOREIGN PATENT DOCUMENTS

| | | | |
|---|---|---|---|
| DE | 36 30 577 A1 | 3/1988 | |
| DE | 102005020561 B4 * | 8/2017 | ................ B01J 2/02 |
| IN | 201747026302 A | 10/2017 | |
| SU | 1071905 A1 | 2/1984 | |
| WO | WO-2016/083617 A1 | 6/2016 | |
| WO | WO-2016/123224 A1 | 8/2016 | |
| WO | WO-2016/156841 A1 | 10/2016 | |
| WO | WO-2016/185053 A1 | 11/2016 | |

OTHER PUBLICATIONS

Duncan, Sylvia H. et al.; "Growth requirements and fermentation products of *Fusobacterium prausnitzii*, and a proposal to reclassify it as *Faecalibacterium prausnitzii* gen. nov., com. nov."; International Journal of Systematic and Evolutionary Microbiology (2002), 52, 2141-2146; Nov. 2002.

Prescott, James K. et al.; "On Powder Flowability"; Pharmaceutical Technology; Oct. 2000; pp. 60-84, 236.

Sanchis, A et al.; "Dielectric Characterization of Bacterial Cells Using Dielectrophoresis"; Bioelectromagnetics 28:393-401 (2007); Apr. 30, 2007.

* cited by examiner

ELECTROSTATIC SPRAY DRYING OF MICROORGANISMS

CROSS-REFERENCE TO RELATED APPLICATIONS

The present application is the U.S. National Stage of International Application No. PCT/EP2021/052136, filed Jan. 29, 2021, and claims priority to European Patent Application 20154883.1, filed Jan. 31, 2020.

The present disclosure relates to methods for electrostatic spray drying of microorganisms and to microorganisms embedded in dried particles.

BACKGROUND OF INVENTION

Spray drying is a technique wherein a suspension is atomized (or sprayed) and thereafter rapidly dried by the use of a gaseous hot drying medium. The scalability of the manufacturing process allows for the formation of particles, destined for use in a wide number of industries, including food, polymer, biotechnology, pharmaceutical or and medical. The choice of atomizer for breaking up the feedstock (suspension) into droplets depends to a large extent on the type of solution and the desired characteristics of the dried particles. Conventional atomizers include rotary atomizers, relying on the use of centrifugal force for droplet formation, hydraulic nozzle atomizers, relying on pressure, and pneumatic nozzle atomizers, relying on kinetic energy. Spray drying has been applied to a wide number of particle types, including bacteria and other microorganisms.

WO16185053 discloses a spray drying method for production of food-grade microparticles comprising the use of a divalent metal salt at mildly acidic conditions for cross-linking an aggregated protein matrix, wherein microorganisms, such as probiotic cells or yeasts, are embedded.

WO16083617 A1 discloses preservation of microorganisms by spray drying followed by freezing in a cryogenic gas.

Electrostatic droplet formation has recently been disclosed as an improved way to achieve droplet formation. The method relies on electrostatically charging the suspension prior to droplet formation. The charging of the suspension may result in improved drying characteristics of the formed droplets and may facilitate particle collection and aggregation. Although electrostatic spray drying offers a significant number of advantages over conventional spray drying, the use and its application to drying of microorganisms has not yet been successful. This is logic as it is known that the viability of microorganisms is affected by electrostatic charges, in fact high voltage is a common method for disinfection of liquids. Consequently, the use of electrostatic spray drying has so far been focused on drying of non-living matter.

US2006071357 discloses a method for formation of microcapsules having a liquid substrate core and a polymeric curable shell, wherein an electric charge is applied to the droplets, ensuring that the droplets do not adhere to the walls of the drying chamber, and further, facilitates collection of the cured particles by the use of an electrostatically charged collection chamber.

U.S. Pat. No. 9,551,527 discloses a method for spray drying of particles wherein the feedstock is charged by the use of a high voltage supply. The drying process of the formed droplets is accelerated due to a resulting coulomb fission process wherein the formed droplets shed smaller daughter droplets due to electrostatic interactions. The document mentions that the method could potentially be applied to the drying of bacteria. However, the method involves the use of highly viscous solutions with low water content, which makes it less efficient for encapsulation of living microorganisms.

U.S. Pat. No. 9,993,787 discloses a method for low-temperature spray drying of specific types of particles in slurries having a low solvent ratio and a high viscosity ratio. The same document further discloses that conventional high-temperature spray drying at above 180° C. may be applied to liquid compositions with a viscosity between 10 and 200 mPa·s and an amount of water between 50-70% by weight.

SUMMARY OF INVENTION

The present inventors have surprisingly realized that electrostatic spray drying can be advantageously used for drying of living microorganisms.

The present disclosure therefore relates to the formation and subsequent drying of electrostatically charged droplets. The droplets are preferably formed from a suspension comprising a living microorganism, a solvent and an additive, wherein the additive may act as a drying protectant. In an embodiment of the present disclosure a two-fluid atomizer is used for formation of the droplets, wherein an atomizing gas is used to promote droplet break-up at the nozzle of the atomizer. Preferably, the droplets are electrostatically charged as a consequence of electrostatically charging of the suspension, prior to formation of the droplets. This may be achieved by contacting the suspension with an electrode having an electric potential difference with respect to ground. Following drying of the droplets, the dried particles are preferably collected, such as by a filter or a sieve.

In a preferred embodiment of the present disclosure the electrostatic charge has been applied such that polar components are forced towards the surface of the droplets, while less polar components of the suspension are forced towards the center of the droplets.

Typically the polarity of the different components have an impact on the resulting electrostatic charge distribution. For example, electrons provided to the suspension are typically associated with the more polar components, usually the solvent, resulting in an electrostatic repulsion between the polar components forcing them towards the surface of the droplets. The similar effect may furthermore act to force the living microorganisms towards the center of the droplets, encapsulated by the additive. Forcing the solvent towards the surface typically results in faster evaporation rates, while embedding the microorganisms in the center of the droplets results in improved encapsulation of the microorganisms.

In another embodiment of the present disclosure the suspension comprises at least 35% by weight water. It is surprising that although the desired end product is dried particles, electrostatic drying of suspensions comprising low amounts of water by weight may be suboptimal. This may be particularly true for drying of sensitive components, such as microorganisms, wherein a high viability of said microorganisms often is desired. An increase in the water content, may act to protect the microorganisms from an electrode, applying the electrostatic charge to the suspension. Furthermore, the increased water content may enable partitioning of the components within the electrostatically charged droplets, wherein the more polar components are forced towards the surface and the less polar components are forced towards the center of the droplets. A low water content, and consequently a high viscosity, of the suspension typically results in a decreased mobility of the components within the droplets. Thereby, a force acting on the components, such as due to the electrostatic charge, may not be sufficient to overcome the large viscosity. As a consequence, the microorganisms may not be efficiently encapsulated by the additive, such as a drying protectant, leading to a low viability. In the same way, the evaporation rate may be lowered at high suspension viscosities, as the solvent may not be present to the same extent at the surface of the droplets.

In yet an embodiment of the present disclosure the microorganism is a strict anaerobic bacterium. Strict anaerobic bacteria, also commonly referred to as obligate anaerobic bacteria, may be killed by normal atmospheric concentrations of oxygen. Therefore, conventional methods cannot be used for production of dried particles comprising viable microorganisms. Contrary to these conventional methods, in an embodiment of the present disclosure all steps of the process are limited. The method is therefore preferably carried out by apparatuses that allow for careful control of the oxygen content. Preferably, all steps are carried out at low oxygen content, including the provision of a suspension, droplet formation, droplet drying and preferably also a collection step for collection of the dried particles.

In an embodiment of the present disclosure the electrostatic charge is applied to the suspension by an electrode in contact with said suspension, and wherein the electrode has a pulsed electric potential difference, with respect to ground. Preferably the electric potential difference, the voltage, has a constant polarity. The electrode may thereby be part of a direct current (DC) circuit wherein current flows in one direction only and the electrode is always kept either negative or positive. The formed droplets may thereby all have an overall negative charge or an overall positive charge. Typically, pulsation of the electric potential difference leads to improved electrical charging of the suspension, and furthermore it may lead to improved characteristics of the dried particles.

In another embodiment of the present invention the electrostatic charge is applied by an electrode in contact with the suspension, and wherein the electrode has an electric potential difference, with respect to ground, below about 40 kV. Preferably the voltage is sufficiently low, such that it does not have a substantial effect of the viability of the microorganisms. Thereby the present disclosure allows for the combination of high viability of the microorganisms in the dried particles, rapid solvent evaporation and efficient encapsulation of the microorganisms.

In yet another embodiment of the present disclosure, the droplets are formed by the use of an atomizing gas, wherein the same gas is used for drying of said droplets by contacting said droplets with the atomizing gas, wherein the atomizing gas is heated to at least 40° C. While the addition of heat to the atomizing gas for formation and drying of sensitive microorganisms may seem counterintuitive, the present inventors have realized that heat can be added to several steps of the process without substantially reducing the viability of the microorganisms.

In an embodiment of the present invention the suspension has a viscosity in the range between about 1 mPa·s to about 10,000 mPa·s. Preferably the viscosity is selected to allow for rapid evaporation of the solvent and efficient encapsulation of the microorganisms. A high viscosity may result in a homogeneous distribution of microorganisms and additives in a dried particle, as a suspension having high viscosity may result in low partitioning, i.e. redistribution, and grouping, of the components within the droplets, based on the polarity of said components.

Preferably the suspension comprises one or more additives. At least part of the additives may be added to the suspension prior to the application of an electrostatic charge to the suspension. The additives are typically provided as a drying protectant wherein said drying protectant acts to stabilize the microorganism within the suspension, the droplets, and/or the dried particles. Preferably, the drying protectant is selected such that it acts to decrease, such as to prevent, killing of said microorganisms, both during the electrostatic spray drying process itself, and during subsequent use of said dried particles and/or the microorganisms, including storage, transport and/or additional processing.

The present invention further relates to a particle comprising living microorganisms embedded in a mass of additives. The particle is preferably compact, such that the particle has a total inner void volume below 5% of the total volume of the particle.

Furthermore, in a preferred embodiment of the present disclosure, the microorganisms are not present at the surface of the particle. Consequently, the microorganisms are preferably embedded within the additive of the dried particles. In an embodiment of the present disclosure, the dried particle comprises substantially a single phase, in addition to the microorganisms. Preferably, the dried particles are thereby not a layered dried particle, such as a dried homogeneous particle encapsulated in a protective layer. In a typical embodiment of the present disclosure, the dried particle has a substantially continuous radial gradient of additive. The dried particles may thereby have a high concentration of additives at the surface, such as 100%. The concentration of additives may continuously decrease towards the center of the particles, thereby forming a radial gradient of additive. Preferably the center of the particles has the highest concentration of microorganisms. In one embodiment of the present disclosure, the dried particles may comprise a living microorganism. The viability of microorganisms is important in many applications, including food, pharmaceutical and medical uses, thus a living microorganism is preferred.

Surprisingly the methods result in dry encapsulated microorganisms with a high level of viability for strict anaerobes as well as for aerobes. The viability is as high as or even higher than for traditional drying methods (spray drying, spray freezing, freeze drying).

DETAILED DESCRIPTION OF THE INVENTION

The present disclosure relates to a process for electrostatic spray drying of a living microorganism, the process comprising the following steps: a. Providing a suspension, comprising a number of components, including a living microorganism, a solvent and an additive; b. Applying an electrostatic charge to said suspension; c. Forming droplets of said suspension; d. Drying said droplets, thereby forming dried particles; and e. (Optionally) collecting the dried particles. Preferably, the droplets are electrostatically charged as a consequence of electrostatically charging of the suspension, prior to formation of the droplets. This may be achieved by contacting the suspension with an electrode having an electric potential difference with respect to ground. Following drying of the droplets, the dried particles are preferably collected, such as at the end of a drying chamber, by one or more filters, one or more sieves and/or, one or more containers.

Preferably the suspension comprises components that have a different dielectric properties. Typically the solvent is more polar than the additive and the microorganism, while the microorganisms are overall less polar than the other two.

In an embodiment of the present disclosure the electrostatic charge has been applied such that polar components are forced towards the surface of the droplets, while less polar components of the suspension are forced towards the center of the droplets. Typically the polarity of the different components have an impact on the resulting electrostatic charge distribution of the formed droplets. For example, electrons provided to the suspension are typically associated with the more polar components, usually the solvent, resulting in an electrostatic repulsion between the polar components forcing the polar solvent and polar additives dissolved in the solvent towards the surface of the droplets. The similar effect may furthermore act to force the microorganisms towards the center of the droplets, encapsulated by the additive. Forcing the solvent towards the surface typically results in faster evaporation rates, while embedding the microorganisms in the center of the droplets results in improved encapsulation of the microorganisms.

In an embodiment of the present disclosure the suspension comprises at least 35% by weight water. It is surprising that although the desired end product is dried particles, electrostatic drying of suspensions comprising low amounts of water by weight may be suboptimal. This may be particularly true for drying of sensitive components, such as microorganisms, wherein a high viability of said microorganisms often is desired. An increase in the water content, may act to protect the microorganisms from an electrode, applying the electrostatic charge to the suspension. Furthermore, the increased water content may enable partitioning of, such as at least partially separating, the components within the electrostatically charged droplets, wherein the more polar components are forced towards the surface and the less polar components are forced towards the center of the droplets and/or dried particles. Thereby, there may be a tendency for the more polar components to be positioned at or near the surface while the tendency of the less polar component is to be positioned at or near the center of the droplets and/or dried particles. A low water content, and consequently a high viscosity, of the suspension, typically results in a decreased mobility of the components within the droplets. Thereby, a force acting on the components, such as due to electrostatic charge, may not be sufficient to overcome the large viscosity. As a consequence, the microorganisms may not be efficiently encapsulated by the additive, such as a drying protectant, leading to a low viability. In the same way, the evaporation rate may be lowered at high suspension viscosities and/or droplet viscosities, as the solvent may not be forced to the same extent to the surface of the droplets, such as the partitioning of the components are slower.

In an embodiment of the present disclosure the microorganism is a strict anaerobic bacterium. Strict anaerobic bacteria, also commonly referred to as obligate anaerobic bacteria, are killed by normal atmospheric concentrations of oxygen. Therefore, viable anaerobic bacteria cannot be spray dried with conventional methods. Preferably, the oxygen content of all steps of the process are limited. The method must therefore be carried out by apparatuses that allow for careful control of the oxygen content. Preferably, all steps are carried out at low oxygen contents, including the provision of a suspension, droplet formation, droplet drying and preferably also a collection step for collection of the dried particles.

In an embodiment of the present disclosure the electrostatic charge is applied to the suspension by an electrode in contact with said suspension, and wherein the electrode has a pulsed electric potential difference, with respect to ground. Preferably the electric potential difference, the voltage, has a constant polarity. The electrode may thereby be part of a direct current (DC) circuit wherein current flows in one direction only and the electrode is always kept negative or positive. The formed droplets may thereby all have an overall negative charge or an overall positive charge. Typically, pulsation of the electric potential difference leads to improved electrical charging of the suspension, and furthermore it may lead to improved characteristics of the dried particles.

In an embodiment of the present invention the electrostatic charge is applied by an electrode in contact with the suspension, and wherein the electrode has an electric potential difference, with respect to ground, below about 40 kV. Preferably the voltage is sufficiently low, such that it does not have a substantial effect of the viability of the microorganisms. Thereby the present disclosure allows for the combination of high viability of the microorganisms in the dried particle, rapid solvent evaporation and efficient encapsulation of the microorganisms.

In yet another embodiment of the present disclosure, the droplets are formed by the use of an atomizing gas, wherein the same gas is used for drying of said droplets by contacting said droplets with the atomizing gas, wherein the atomizing gas is heated to at least 40° C. While the addition of heat to the atomizing gas for formation and drying of sensitive microorganisms may seem counterintuitive, the present inventors have realized that heat can be added to several steps of the process without substantially affecting the viability of the microorganisms.

In an embodiment of the present invention the suspension has a viscosity in the range between about 1 mPa·s to about 10,000 mPa·s. Preferably the viscosity is selected to allow for rapid evaporation of the solvent and efficient encapsulation of the microorganisms. A high viscosity may result in a homogeneous distribution of microorganisms and additives in a dried particle, as a suspension having high viscosity may result in low partitioning, i.e. redistribution, and grouping, of the components within the droplets, based on the polarity of said components. The redistribution leads to essentially complete encapsulation of microorganisms within the interior of the particles.

Preferably the suspension comprises one or more additives. At least part of the additives may be added to the suspension prior to the application of an electrostatic charge to the suspension. The additives are typically provided as a drying protectant wherein said drying protectant acts to stabilize the microorganism within the suspension, the droplets, and/or the dried particles. Preferably, the drying protectant is selected such that is act to decrease, such as to prevent, killing of said microorganisms, both during the electrostatic spray drying process itself, but also during subsequent use of said dried particles and/or the microorganisms, including storage, transport and/or additional processing.

The present invention further relates to a particle comprising living microorganisms embedded in a mass of additives. The particle is preferably compact, such that the particle has a total inner void volume below 5% of the total volume of the particle. Furthermore, in a preferred embodiment of the present disclosure, the microorganisms are not present at the surface of the particle. Consequently, the microorganisms are preferably embedded within the additive of the dried particles. In an embodiment of the present disclosure, the dried particle comprises substantially a single phase, in addition to the microorganisms. Preferably, the dried particles are thereby not a layered dried particle, such as a dried homogeneous particle encapsulated in a protective layer. In a typical embodiment of the present disclosure, the dried particle has a substantially continuous radial gradient of additives. The dried particles may thereby have a high concentration of additives at the surface, such as 100%. The concentration of additives may continuously decrease towards the center of the particles, thereby forming a radial gradient of additives. Preferably the center of the particles has the highest concentration of microorganisms.

In one embodiment of the present disclosure, the dried particles may comprise a living microorganism. The viability of microorganisms is important in many applications, including food, pharmaceutical and medical uses, thus a living microorganism is preferred.

Electrostatic Charging

In an embodiment of the present disclosure the electrostatic charge is applied to the suspension by contacting said suspension with at least one electrode having an electric potential difference with respect to ground, a voltage. The electrode may therefore be provided in a configuration for applying said voltage to said suspension. Additional electrodes may be provided, such as two, or three, or four, or even additional electrodes for applying said electrostatic charge to said suspension. Preferably the two or more electrodes have the same polarity, such as positive or negative voltage, as given for example in a direct current circuit. Configurations of electrodes for applying an electrostatic charge are known by a person skilled in the art, and may include the use of specific materials, surface area, and shape of the one or more electrodes.

In an embodiment of the present disclosure the electrode has an electric potential difference, with respect to ground, below about 40 kV, such as below about 35 kV, such as below about 30 kV, such as below about 25 kV, such as below about 20 kV, such as below about 15 kV, such as below about 10 kV. Preferably the voltage is sufficiently low in order to not cause any damage to the microorganisms. Thereby, the voltage should be sufficiently low in order to not kill the living microorganisms.

In an embodiment of the present disclosure the electrode has a fixed polarity, with respect to ground, such as fixed negative polarity or fixed positive polarity. The electrode, or the multiple electrodes, may therefore be configured for applying a direct circuit (DC) voltage. Preferably, the electrode(s) is configured for a continuous supply of electrons, or a continuous drain of electrons, to/from the suspension. Typically, a positive electrode, an anode, drains a suspension of electrons while a negative electrode, a cathode, supplies a suspension with electrons. The electrode may temporarily have a ground potential, i.e. 0 V.

In an embodiment of the present disclosure the electric potential difference, with respect to ground, of the electrode is constant. The voltage of the electrode may thereby be constant, and consequently, the electrostatic charge may be delivered to the suspension by the use of a constant voltage.

In another embodiment of the present disclosure the electric potential difference, with respect to ground, of the electrode varies over time, such as in periodic variations. The periodic variations may be described by a wave function, such as by a sinus wave, or a combination of multiple wave functions, combined to make a periodic variation. The periodic variations may be described by two or more voltage levels, which the voltage of the electrode varies, in cyclic variations. One of the voltage levels may be ground.

In an embodiment of the present disclosure the electric potential difference, with respect to ground, of the electrode varies periodically, such as in a periodic step function. The voltage of the electrode may vary according to any function and may furthermore depend on parameters of the method, such as the feed rate of the suspension, the droplet sizes, the contents of suspension, such as the type of components and their relative ratios, and furthermore desired parameters of the dried particles.

In an embodiment of the present disclosure the electric potential of the electrode is applied by pulse width modulation, such as by a square wave. The voltage of the electrode may as a consequence vary between two or more set levels, forming a square wave, wherein the time between two pulses may be a set value or may vary depending on parameters of the processing method as mentioned elsewhere herein. The voltage may be provided as a pulse between two or more voltage values, wherein the dwell time at each level may be set individually, and wherein one of the voltage levels may be 0 V.

In an embodiment of the present disclosure the components of the suspension are partitioned within the formed droplets with respect to their polarity, such as for increased evaporation of the solvent and/or increased encapsulation of the microorganism. Partitioning of components of the suspension may lead to advantageous properties of the formed droplets, such as increased evaporation, e.g. decrease evaporation time and/or less water content in the final dried particles, and/or improved encapsulation of the dried particles. Consequently, components of the suspension may be chosen based on how they are partitioned within a formed droplet, such as in an electrostatically charged formed droplet.

In an embodiment of the present disclosure the components of the suspension of higher polarity are partitioned to the surface of the droplets and components of the suspension of lower polarity are partitioned to the center of the droplets. In an embodiment of the present disclosure at least two components of said suspension have different dielectric properties. Preferably, there is a relationship between the partitioning of the components of the suspension, within the droplets, and the dielectric properties and/or the effective dielectric properties, of said components of the suspension.

In an embodiment of the present disclosure the microorganism has a lower effective dielectric property than the additive and/or the solvent. In an embodiment of the present disclosure the solvent has a higher dielectric constant than the additive, and the additive has a higher dielectric constant than the microorganism. Among the solvent, the additives and the microorganism, it is preferred that the solvent has the highest dielectric property, while the additive has a higher dielectric property than the microorganisms. The dielectric property of the microorganisms may be measured and/or given as an effective dielectric property, wherein the overall dielectric property of the microorganism is given, and not the dielectric property of individual components, such as specific membrane proteins, as known by a person skilled in the art, for example in Sanchis et al., Dielectric characterization of bacterial cells using dielectrophoresis, Bioelectromagnetics, 2007.

Bacteria

In a preferred embodiment of the present disclosure the suspension comprises living microorganisms. Living microorganisms are used in a wide range of areas including medicine, biotechnology, food, pharmaceutics, material industries. The industry of probiotics, for example, relies on the provision of live bacteria for stimulation of the microbiome. Furthermore, fecal microbiota transplant, has recently gained widespread recognition, wherein the microbiome of healthy donors are administered to individuals that suffer from any of the numerous microbiome related diseases. Administering may be in the digestible capsule comprising dried particles comprising a microorganism, such as bacteria. In an embodiment of the present disclosure, the microorganism is selected from the microorganisms normally present in the human microbiome and may additional to bacteria include other types of microorganisms, such as archaea, fungi, protists and viruses.

In an embodiment of the present disclosure, the suspension comprises a species of anaerobic bacteria. In an embodiment of the present disclosure the suspension comprises a species of facultative anaerobic bacteria, a species of aerotolerant anaerobic bacteria, a species of obligate anaerobic bacteria, or a species of strict anaerobic bacteria, or a mixture thereof. The microorganisms may be facultative anaerobes, aerotolerant anaerobes, obligate anaerobes, strict anaerobes, or a mixture thereof. As known to a person skilled in the art, the oxygen level affects the ability of growth, or for some types of bacteria, even the ability of survival. Depending on the type of bacteria, it may be a requirement that the oxygen content is above or below a certain level for growth and/or survival. Therefore, in a preferred embodiment of the present disclosure the oxygen content is controlled, for growth and/or survival of the bacteria.

In an embodiment of the present disclosure the suspension comprises a species of strict anaerobic bacteria. A strict anaerobe, also known as an obligate anaerobe, is a bacterium that may be killed by normal atmospheric levels of oxygen. This may be attributed to several factors, mainly related to how oxygen interacts with biochemical processes in the microorganisms. Strict anaerobes may include spore-forming bacteria, wherein the bacteria can survive in their dormant form at atmospheric levels of oxygen. Strict anaerobe bacterial genera include *Actinomyces, Bacteroides, Clostridium, Eubacterium, Fusobacterium, Peptostreptococcus, Porphyromonas, Prevotella, Propionibacterium,* and *Veillonella.*

In an embodiment of the present disclosure the microorganism is selected from the group consisting of a facultative anaerobic bacteria, such as *Lactococcus* sp. or *Lactobacillus* sp., or a strict anaerobic bacteria, such as *Bacteroides* sp., *Faecalibacterium* sp., or *Eubacterium* sp. Lactic acid bacteria, such as *Lactococcus* and *Lactobacillus*, are advantageously used in the food industry for industrial dairy fermentation, such as for dairy production. Furthermore, *Faecalibacterium* is one of the most abundant and important commensal bacteria of the human gut microbiota.

In an embodiment of the present disclosure the suspension comprises at least one species of strict anaerobic bacteria selected from the group consisting of *Adlercreutzia* sp., *Akkermansia* sp., *Alistipes* sp., *Anaerotruncus* sp., *Bacteroidales, Bacteroides* sp., *Blautia* sp., *Butyricicoccus* sp., *Butyrivibrio* sp., *Catabacteriaceae* sp., *Christensenella* sp., *Clostridiales* sp., *Clostridium* sp., *Collinsella* sp., *Coprococcus* sp., *Cutibacterium* sp., *Dialister* sp., *Dorea* sp., *Erysipelotrichaceae* sp. *Eubacterium* sp., *Faecalibacterium* sp., *Flavonifractor* sp., *Fusobacterium* sp., *Hafnia* sp., *Holdemania* sp., *Hungatella* sp., *Intestinibacter* sp., *Lachnobacterium* sp., *Lachnospira* sp., *Lachnospiraceae* sp, *Lachnospiraceae* gen. nov. sp. nov, *Lachnospiraceae* sp. nov., *Methanobrevibacter* sp., *Methanomassiliicoccus* sp., *Methanosarcina* sp., *Mitsuokella* sp., *Odoribacter* sp., *Oscillospira* sp., *Oxalobacter* sp., *Parabacteroides* sp., *Phasco-*

*larctobacterium* sp., *Porphyromonadaceae* sp., *Prevotella* sp., *Propionibacterium* sp., *Rikenellaceae* sp., *Roseburia* sp., *Ruminococcus* sp., *Subdoligranulum* sp., *Sutterella* sp., *Turicibacteraceae* sp.

In an embodiment of the present invention, the microorganism has a dielectric constant, such as an effective dielectric constant, below 20, such as below 15, such as below 10, such as below 8. One or more components of the suspension may be selected based on their dielectric constants. Preferably, one or more components, additional to the microorganism, is selected based on the dielectric constant, such as the effective dielectric constant of the microorganism. The dielectric constants of microorganisms are described in the literature, such as Ferrer, 2014, "Electric polarization properties of single bacteria measured with electrostatic force microscopy". Typically, gram positive bacteria have a higher (effective) dielectric constant than gram negative bacteria. Components of the suspension, additional to the microorganism, may therefore be selected based on the microorganism, such as the effective dielectric properties, of the microorganism to be dried.

In an embodiment of the present disclosure the suspension comprises at least one species of strict anaerobic bacteria selected from the group consisting of *Adlercreutzia* sp., *Adlercreutzia equolifaciens, Akkermansia* sp., *Akkermansia muciniphila, Alistipes* sp., *Alistipes finegoldii, Alistipes hadrus, Alistipes indistinctii, Alistipes onkerdonkii, Alistipes putredinis Alistipes shahii, Anaerostipes* sp. *Anaerostipes caccae, Anaerostipes hadrus, Anaerotruncus* sp., *Bacteroidales, Bacteroides* sp., *Bacteroides dorei, Bacteroides fragilis, Bacteroides intestinalis, Bacteroides intestinihominis, Bacteroides ovatus, Bacteroides putredinis, Bacteroides thetaiotaomicron, Bacteroides uniformis, Bacteroides vulgatus, Bacteroides xylanisolvens, Blautia* sp, *Blautia luti, Blautia obeum, Blautia wexlerae, Butyricicoccus, Butyrivibrio fibrisolvens, Butyrivibrio* sp., *Catabacteriaceae, Christensenella* sp., *Clostridiales, Clostridium* sp., *Clostridium scindens, Clostridium spiroforme, Clostridium butyricum, Collinsella* sp., *Collinsella aerofaciens, Coprococcus* sp., *Coprococcus catus, Coprococcus comes, Coprococcus eutactus, Coprococcus* sp., *Cutibacterium acnes, Dialister* sp., *Dialister invisus, Dorea* sp., *Dorea formicigenerans, Dorea longicatena, Erysipelotrichaceae, Eubacterium* sp. *Eubacterium eligens, Eubacterium hallii, Eubacterium limosum, Eubacterium ramulus, Eubacterium rectale, Eubacterium siraeum, Eubacterium ventriosum, Faecalibacterium* sp., *Faecalibacterium prausnitzii, Flavonifractor plautii, Fusobacterium prausnitzii, Hafnia, Holdemania, Hungatella hathewayi, Intestinibacter bartlettii, Lachnobacterium, Lachnospira, Lachnospira pectinoshiza, Lachnospiraceae, Lachnospiraceae* gen. nov. sp. nov, *Lachnospiraceae* sp. nov., *Methanobrevibacter* sp., *Methanomassiliicoccus* sp., *Methanosarcina, Mitsuokella multiacidus, Odoribacter, Oscillospira, Oxalobacter formigenes, Parabacteroides* sp., *Parabacteroides distasonis, Phascolarctobacterium, Porphyromonadaceae, Prevotella* sp., *Prevotella albensis, Prevotella amnii, Prevotella bergensis, Prevotella bivia, Prevotella brevis, Prevotella bryantii, Prevotella buccae, Prevotella buccalis, Prevotella copri, Prevotella dentalis, Prevotella denticola, Prevotella disiens, Prevotella histicola, Prevotella intermedia, Prevotella maculosa, Prevotella marshii, Prevotella melaninogenica, Prevotella micans, Prevotella multiformis, Prevotella nigrescens, Prevotella oralis, Prevotella oris, Prevotella oulorum, Prevotella pallens, Prevotella salivae, Prevotella stercorea, Prevotella tannerae, Prevotella timonensis, Prevotella veroralis, Propionibacterium acnes,*

*Rikenellaceae, Roseburia* sp. *Roseburia faecis, Roseburia hominis, Roseburia intestinalis, Roseburia inulinivorans, Ruminococcus* sp., *Ruminococcus bicirculans, Ruminococcus gauvreauii, Ruminococcus gnavus, Ruminococcus lactaris, Ruminococcus obeum, Ruminococcus torques, Ruminococcus albus, Ruminococcus bromii, Ruminococcus callidus, Ruminococcus flavefaciens, Ruminococcus gauvreauii, Subdoligranulum, Sutterella* and *Turicibacteraceae.*

In an embodiment of the present disclosure the suspension comprises an anaerobic bacteria selected from the group consisting of *Akkermansia, Bacteroides, Bifidobacterium, Faecalibacterium, Lactobacillus, Eubacterium.*

In an embodiment of the present disclosure the suspension comprises a gram positive bacteria selected from the list including *Eubacterium* spp., *Lactococcus* spp., *Streptococcus* spp., *Lactobacillus* spp., *Leuconostoc* spp., *Pseudoleuconostoc* spp., *Pediococcus* spp., *Brevibacterium* spp., *Enterococcus* spp., *Propionibacterium* spp., *Bifidobacterium* spp, *Bacillus* spp.

In an embodiment of the present disclosure the suspension comprises a yeast.

In an embodiment of the present disclosure the suspension comprises a spore forming bacteria, such as *Bacillus subtilis* sp.

Droplets

In an embodiment of the present disclosure the droplets are formed by atomizing the suspension. Atomizing and spraying may be used interchangeably herein as referring to the process of forming multiple small droplets of a liquid, such as a suspension, from a larger volume, such as a feedstock. Droplet formation, i.e. the breakup of a liquid volume into smaller droplets requires energy, due to the increase in surface area. The interfacial energy, typically given at the liquid-air interface at the surface of the droplets, requires the addition of energy for formation. As known to a person skilled in the art, the energy may be supplied in a wide range of ways.

In an embodiment of the present disclosure the formation of droplets is carried out by means of an atomizing device, such as an ultrasound nozzle; a pressure nozzle; a two-fluid nozzle (e.g. using CO2 or N2 or other gases as atomizing gas); a vibrating nozzle; a frequency nozzle, an electrostatic nozzle; or a rotating atomizing device. Different types of nozzles are known to a person skilled in the art, and they may have their individual advantages. Several parameters can be adjusted based on the desired properties of the droplets, and consequently the dried particles, including the flow rates of an atomizing gas, the flow rate of the suspension/feedstock, the use of surfactants, the configuration of the nozzle, the type of nozzle, the forces acting on the suspension (gravity, electrical, centrifugal or other).

In an embodiment of the present disclosure the formation of droplets is carried out by means of a two-fluid nozzle. Two-fluid nozzles atomize a liquid, such as a suspension, by an interaction between a high velocity gas and a liquid, such as a suspension. Typically compressed air is used as an atomizing gas, but other gases, such as steam may be used. A two-fluid nozzle may be of an internal mix type or an external mix type depending on the mixing point of the gas and liquid streams relative to the nozzle face.

Atomizing Gas

In an embodiment of the present disclosure the formation of droplets in step c) is performed using an atomizing gas. Preferably the atomization of the droplets is performed by the use of a two-fluid nozzle configured for droplet formation by the use of said atomizing gas.

In an embodiment of the present disclosure the atomizing gas is selected from the group consisting of an inert gas (such as Nitrogen and Carbon dioxide), a noble gas (e.g. Helium, Argon or Neon), and an alkane gas (such methane), or a mixture thereof.

In an embodiment of the present disclosure the atomizing gas comprises or consists of Nitrogen, Carbon Dioxide and/or atmospheric gas, or a mixture thereof. The gas may be treated before use in any suitable way including filtered, sterilized, and/or dehumidified. However, in an embodiment of the present disclosure the atomizing gas has not been dehumidified. The use of non-dehumidified gas may be advantageous in several aspects, including providing a simpler operation, decreasing cost and time, and may furthermore lead to better droplet and/or dried particle characteristics.

In an embodiment of the present disclosure the atomizing gas has a moisture content below about 1000 ppm, such as below about 500 ppm, such as about below 100 ppm, such as about below 50 ppm, such as about below 10 ppm.

In an embodiment of the present disclosure the droplet forming step, (e.g. the spray step) is carried out with an atomizing gas inlet temperature of at most about 200° C., such as in the range between about 20° C. to about 200° C., such as in the range between about 40° C. to about 150° C., or such as in the range between about 40° C. to about 120° C., such as between about 40° C. to about 90° C., such as between about 50° C. to about 90° C., such as between about 60° C. to about 85° C., such as about 80° C. It may be desirable to have an elevated temperature, with respect to normal room temperature for optimal droplet formation, solvent evaporation and/or dried particle characteristics. However, an increased temperature may at the same time be detrimental for components of the suspension, such as the microorganisms. Therefore, the optimal temperature may not only be based on easiest mode of performing said process, such as at room temperature, but instead may be a contribution of multiple factors, including ease of performing said process, rapid evaporation, viability of the living microorganisms, specific characteristics of the dried particles, such as optical encapsulation of the microorganisms, a sufficiently low volume of gas-filled voids within the dried particles (compactness of the dried particles) and other parameters. Consequently, the optimal temperature is non-trivial and is based on several factors. Preferably the temperature is above room temperature, such as for rapid evaporation, but below a temperature detrimental to the microorganisms, given the specific temperature experienced by said microorganisms, as it is preferably thermally isolated during drying, by being embedded within the additive and, at least temporarily, the solvent. The temperature may consequently, be within the range of between about 20° C. to about 200° C.

In an embodiment of the present disclosure the atomizing gas has an inlet pressure in the range between about 1 kPa to about 500 kPa, such as in the range between about 5 kPa to about 500 kPa, such as in the range between about 5 kPa to about 300 kPa, such as in the range between about 5 kPa to about 100 kPa, such as about 60 kPa, or such as about 70 kPa, or such as about 80 kPa, or such as in the range between about 100 kPa to about 400 kPa, such as about 120 kPa, or about 150 kPa, or about 200 kPa, or about 250 kPa, or about 300 kPa, or about 350 kPa.

In an embodiment of the present disclosure the atomizing gas has an inlet pressure in the range between about 50 kPa to about 400 kPa. Typically, the inlet pressure of the atomizing gas is defined as the pressure of said atomizing gas before being supplied to the nozzle, such as the two-fluid nozzle. Typically, the inlet pressure of the atomizing gas is the pressure of said atomizing gas supplied to a spray drying apparatus, such as an electrostatic spray drying apparatus. The gas may be supplied from a gas tank comprising at least one pressure regulator, for controlling the pressure provided to said spray dryer and/or said nozzle. Preferably, the pressure supplied to the nozzle is substantially the same as the inlet pressure. Following formation of droplets, the pressure of the atomizing gas decreases, typically due to high resistance in the atomizing nozzle in combination with a large cross section of the drying chamber.

Feedstock

In an embodiment of the present disclosure the suspension has a viscosity in the range between about 1 mPa·s to about 10,000 mPa·s, such as in the range between about 10 mPa·s to about 5,000 mPa·s, such as in the range between about 50 mPa·s to about 5,000 mPa·s, such as in the range between about 50 mPa·s to about 3,000 mPa·s, such as in the range between about 50 mPa·s to about 1,000 mPa·s, such as in the range between about 50 mPa·s to about 500 mPa·s, such as in the range between about 70 mPa·s to about 300 mPa·s, such as about 100 mPa·s.

The pH of the feedstock or suspension can vary within the limits not negatively affecting the viability of the microorganisms significantly. Preferably the pH is between 4 and 8, for example 4-5, 5-6, 6-7, or 7-8.

In an embodiment of the present disclosure the solvent comprises or consists of water. The solvent, such as water, may be derived from a culture medium wherein the microorganisms have been cultured, alternatively or additionally the solvent, such as water, may have been added for formation of the suspension.

In an embodiment of the present disclosure the suspension comprises at least 35% by weight water, such as at least 40% by weight water, such as at least 50% by weight water, such as at least 60% by weight water, such as at least 70% by weight water, such as at least 80% by weight water, such as at least 90% water, for example up to 95%. It may be a preference to not have the water content of the suspension below 35% by weight. This may seem counter intuitive, as the end product is a dried particle. However, several characteristics of the final dried particles, may be improved by a water content of at least 35% by weight of the suspension, such as at least 50% by weight water, such as at least 70% by weight water. For example, partitioning of components of the suspension within a droplet relies on the reposition of said components within the droplets. The repositioning may be driven by the electrostatic interactions between components (the same type of components, or different types of components) of the suspension. This may be a result of the electrostatic charge of the droplets, that may in itself be a result of electrostatically charging of the suspension after, during and/or before droplet formation. Preferably, the electrostatically charge is added to the suspension by an electrode in contact with said suspension, before droplet formation. The electrostatic charge of said formed droplets may result in more polar components being forced towards the surface of said droplets while less polar components being forced towards the center of said droplets. Thereby a gradient may be formed within the droplets, based on the polarity (or the effective dielectric properties) of the components of the suspension. This may be a result of more polar components of said suspension being, in general, more susceptible to accepting, or donating—depending on the polarity of said electron, electrons from said electrode, while less polar components, in general, are less susceptible to accepting, or donating, electrons to said electrode. Even though a force may be applied to the components of the suspension, within a droplet, acting to reposition the components, the components may not be repositioned fully, such as according to their polarity—typically wherein the solvent are driven towards the surface of said droplets and the microorganisms are driven towards the center of said droplets. Instead the components may only be repositioned partly, or substantially not at all. This may be attributed to the viscosity of the suspension, typically the viscosity of the suspension before drying, as this is the viscosity of a newly formed droplet. The viscosity of a newly formed droplet affects the repositioning of components of the suspension within said droplet. A higher viscosity in general decreases the mobility of said components and, thereby, the components may not be repositioned, or only repositioned to a limited degree. Therefore, while the final product is a dried particle, in a preferred embodiment of the present disclosure the suspension comprises at least 35% of water by weight. Unless otherwise specified, the suspension refers to the feedstock of which droplets are formed. While the same suspension may be present in the droplets, the solvent (water) content during drying is, naturally, decreasing overtime.

In an embodiment of the present disclosure the suspension comprises the additive in the range between about 5% by weight to about 60% by weight, such as in the range between about 5% by weight to about 50% by weight, such as in the range between about 5% by weight to about 40% by weight, such as in the range between about 5% by weight to about 30% by weight, such as in the range between about 5% by weight to about 20% by weight, such as about 10% by weight.

In an embodiment of the present disclosure the suspension comprises the microorganism in the range between about 10% by weight to about 60% by weight, such as in the range between about 15% by weight to about 50% by weight, such as in the range between about 15% by weight to about 40% by weight, such as in the range between about 15% by weight to about 30% by weight, such as about 20% by weight.

In an embodiment of the present disclosure the suspension comprises solvent, microorganisms and an additive in the range between about 40-85:10-60:5-60 respectively, such as in the range between about 50-75:20-50:10-40 respectively, such as in the range between about 55-70:20-40:10-30 respectively, such as in the range between about 55-65:20-30:10-20 respectively, such as about 60:30:10 respectively.

Mode of Transport

In an embodiment of the present disclosure the droplets are dried in a drying chamber and wherein the major accelerating force(s), for movement of the droplets through the drying chamber, is gravity and/or forces due to interactions with the spray gas, such as drag force. Typically the main driving force for movement of the formed droplets is the atomizing gas acting to both form the droplets, but furthermore to drive the formed droplets forwards, such as towards the outlet end of a drying chamber. While gravity may have an effect on the transportation of the droplets, the effect is typically negligible in comparison with the force exerted by the atomizing gas. Typically, as known to a person skilled in the art, the atomizing gas may be supplied at an angle with respect to the droplet formation for swirling the formed droplets within the drying chamber, typically for prolonging the drying time.

In an embodiment of the present disclosure the droplets are dried in a drying chamber and wherein the major accelerating force(s), for movement of the droplets through the drying chamber, is not due to electrostatic interactions with electric fields. Preferably the electric field within the drying chamber is sufficiently low to not have a substantial effect on the trajectory of the droplets. An electric field may have a negative impact on the process, for example the partitioning of components of the suspension, due to electrostatic interactions, may be impeded due to an electric field acting on the particles. Upon repositioning of the components of the suspension, an electric field may not lead to a radial gradient of the components, as is typically preferred, instead an electrical field may attract one or more certain components of the suspension to a fraction of the surface of the droplet, resulting in a decreased evaporation rate and an impaired encapsulation of the microorganisms, that may result in a decreased viability.

In an embodiment of the present disclosure the movement of droplets through the drying chamber is substantially not due to interaction with an electrical field. Electrical fields may typically be used in spray dryers for droplet formation or for controlling the trajectory of the formed droplets, such as to not immobilize on the surface of the drying chamber. The droplet trajectory may however be controlled with other means, if desired, such as by gravity or by a gas flow, such as by the atomizing gas or additional gases introduced for controlling the trajectory of the formed droplets/dried particles.

Drying Protectant

In an embodiment of the present disclosure the suspension comprises one or more additives, such as a stabilizing additive. Typically drying of microorganisms require stabilization for drying In an embodiment of the present disclosure the one or more additives are added to the suspension prior to step c), such as prior to step b) or step a) or at multiple points before step c). The additive may thereby be added at any point prior to the formation of the droplets. The additive may furthermore be a remnant from a suspension used in an earlier process. Such an additive used for culturing of the microorganisms. Alternatively or additionally, the additive may be added to the suspension wherein the additive is selected for stabilization of the microorganism upon drying of said microorganisms, such as by using an electrostatic spray dryer apparatus.

In an embodiment of the present disclosure the one or more additives is selected from the group consisting of: Inositol, lactose, sucrose, trehalose, inulin, maltodextrin, dextrose, alginate or a salt thereof (e.g. sodium alginate), skimmed milk powder, yeast extract, casein peptone, hydrolyzed protein, such as hydrolyzed casein, casein or salts thereof (such as sodium caseinate), inosine, inosinemonophospate and a salt thereof, glutamine and salts thereof (such as monosodium glutaminate), ascorbic acid and salts thereof (such as sodium ascorbate), citric acid and salts thereof, polysorbate, a hydrate of Magnesium sulphate (e.g. a heptahydrate), a hydrate of Manganous sulphate (e.g. a monohydrate) and Dipotassium hydrogen phosphate, propyl gallate or a mixture thereof.

In an embodiment of the present disclosure the additive comprises a drying protectant selected from the group including cyclitols, such as inositol, and monosaccharide, such as dextrose, disaccharides such as lactose, sucrose and trehalose, polysaccharides (oligosaccharides), such as inulin, maltodextrin and starch, magnesium stearate, peptides, proteins, sugar alcohols, such as mannitol, sorbitol, or hydrogenated starch hydrolysates, fatty acid esters, alginate or a salt thereof (e.g. sodium alginate) or a mixture thereof.

In an embodiment of the present disclosure the encapsulation index, defined as the weight ratio between the microorganism and the drying protectant, is in the range between about 1:0 to about 1:10, such as in the range between about 1:1 to about 1:9, such as in the range between about 1:1 to about 1:7, such as in the range between about 1:1 to about 1:5, such as in the range between about 1:1 to about 1:3. The encapsulation index may thereby directly relate to the weight ratio between the drying protectant and the microorganisms of the formed droplet as well as that of the dried particles. While the use of drying protectant is optional, it may be preferred, depending on for example the specific type of microorganism to be dried.

In an embodiment of the present disclosure the dried particle comprises the drying protectant in the range between about 0% by weight to about 95% by weight, such as between about 50% by weight to about 90% by weight, such as between about 50% by weight to about 85% by weight, such as between about 50% by weight to about 80% by weight, such as between about 50% by weight to about 75% by weight.

The process according to any one of the preceding claims, wherein the one or more additive is selected from the group consisting of Yeast Extract, Dextrose, Polysorbate, Dipotassium hydrogen phosphate, Magnesium sulphate heptahydrate, Manganous sulphate monohydrate.

In an embodiment of the present disclosure the one or more additive is selected from the group consisting of Yeast Extract, Dextrose, Polysorbate, Dipotassium hydrogen phosphate, Magnesium sulphate heptahydrate, Manganous sulphate monohydrate and optionally a mixture of vitamins.

In an embodiment of the present disclosure the drying protectant comprises or consists of equal weights of trehalose and maltodextrin.

In an embodiment of the present disclosure the amount of emulsifier, by weight, of the suspension is below about 5%, such as below about 3%, such as below about 2%, such as below about 1%, such as about 0%, such as 0%. While emulsifier typically decreases the interfacial tension and promotes droplet formation, the use of emulsifiers at high levels can have detrimental effects to an electrostatic spray drying process, for example the emulsifiers may prevent partitioning of components of the suspension, within the formed droplets, thereby potentially leading to a decrease in the evaporation rate and the viability of the microorganisms upon drying. Furthermore, emulsifiers may affect the function and/or the viability of microorganisms. In an alternative embodiment of the present disclosure, the surfactant is a non-ionic surfactant.

Optional Other Prior Steps

In an embodiment of the present disclosure the microorganism is an anaerobic bacteria and all steps, from cultivation to collection of dried particles, are carried out in the presence of less than about 5% oxygen, such as less than about 2% oxygen, preferably less than about 1% oxygen, such as 0.5% oxygen, such as less than about 0.05% oxygen. The specific oxygen content during the process may be chosen based on the type of microorganism, such as a strict anaerobe or a facultative anaerobe. Furthermore, not necessarily all steps need to be at the same oxygen content level. For example, a microorganism may be more tolerable to oxygen under certain conditions, as known to a person skilled in the art, and thereby given that a specific condition is present, a step may be performed at a different oxygen content level.

In an embodiment of the present disclosure the microorganism is an anaerobic bacteria and all steps, from cultivation to collection of dried particles, are carried out in the presence of less than about 0.5% oxygen, such as less than about 0.25% oxygen, such as less than about 0.1% oxygen, such as less than about 0.05% (about 5 ppm) oxygen, such as less than about 0.02% oxygen, or less than about 0.03% oxygen, or less than about 0.04% oxygen.

In an embodiment of the present disclosure the microorganism is an anaerobic bacteria and all steps, from cultivation to collection of dried particles, are carried out in the presence of oxygen in the range between about 0.0001% to about 2% oxygen, such as in the range of about 0.0001% to about 0.5% oxygen, such as in the range between about 0.001% to about 0.05% oxygen, e.g. in the range between about 0.001% to about 0.025% oxygen, such as about 0.01% oxygen, or such as about 0.02% oxygen, or in the range between about 0.025% to about 0.05% oxygen, such as about 0.03% oxygen, or such as about 0.04% oxygen.

In an embodiment of the present disclosure the microorganism is an anaerobic bacteria and all steps, from cultivation to collection of dried particles, are carried out under essentially anaerobic conditions. The microorganism may therefore be a strict anaerobe bacteria.

In an embodiment of the present disclosure the process comprises a concentrating step prior to step b), such as prior to step a). The suspension may thereby be provided as a concentrated suspension, wherein the concentration, such as the number per volume, of microorganisms are increased with respect to an earlier state of the suspension. For example, it may be desired to increase the concentration of microorganisms in the suspension with respect to the number of microorganisms in a prior culturing step of said microorganisms, where applicable. Therefore, the presence of a concentration step may be related to the concentration of microorganisms in a fluid in an earlier step, such as prior to formation of the suspension.

In an embodiment of the present disclosure the process further comprises a fermentation step prior to step b), such as prior to step a).

In an embodiment of the present disclosure the process comprises a washing step prior to step b, such as prior to step a), wherein a suspension of microorganisms (e.g. bacteria) is washed to remove components, at least partly, from the suspension of microorganism, e.g. components of the culture medium. Components that are undesirable to form part of the suspension are thereby preferably washed away, completely or partly. The washing step may as a consequence, be used for washing away non-living/non-viable microorganisms, for increasing the number of living/viable microorganisms in the suspension, and as a consequence the final dried particles.

In an embodiment of the present disclosure the process comprises a fermentation step, a concentration step, and the process steps a) to b), or process steps a) to c), or process steps a) to d), or process steps a) to e), which are all performed in the presence of no more than 0.5% oxygen, such as less than 0.05% oxygen.

In an embodiment of the present disclosure the process comprises a fermentation step, a concentration step, and the process steps a) to b), or process steps a) to c), or process steps a) to d), or process steps a) to e), which are all performed under essentially anaerobic conditions.

In an embodiment of the present disclosure the process comprises a fermentation step, concentration step, a washing step, and the process steps a) to b), or process steps a) to c), or process steps a) to d), or process steps a) to e), which are all performed in the presence of no more than 0.5% oxygen, such as less than 0.05% oxygen.

In an embodiment of the present disclosure the process comprises a fermentation step, concentration step, a washing step, and the process steps a) to b), or process steps a) to c), or process steps a) to d), or process steps a) to e), which are all performed under essentially anaerobic conditions.

Particle Drying

In an embodiment of the present disclosure the dried particles have a size from about 1 micrometer to about 800 micrometers, such as in the range from about 5 micrometers to about 800 micrometers, such as about 10 micrometers to about 600 micrometers, such as about 10 micrometers to about 300 micrometers, such as about 10 micrometers to about 200 micrometers, such as about 10 micrometers to about 50 micrometers, or such as about 50 micrometers to about 200 micrometers, such as about 50 micrometers to about 100 micrometers, such as about 75 micrometers, or such as about 100 micrometers to about 200 micrometers, such as about 150 micrometers, measured as Dv50 values. As known to a person skilled in the art Dv50 is typically used for referring to the median of a volume distribution.

In an embodiment of the present disclosure the size distribution of the dried particles is substantially unimodal.

In an embodiment of the present disclosure the dried particles are substantially dry. Small amounts of solvent, such as trace amounts of solvent, may be present in the dried particles. Therefore in an embodiment of the present disclosure the process comprising a drying step for drying the formed droplets.

In an embodiment of the present disclosure the process comprising a drying step, and wherein the drying of the droplets takes place under reduced pressure. A reduced pressure may be used in order to improve the evaporation, such as to increase the evaporation rate, and furthermore to control or steer the dried particles into a dedicated collector at an outlet end of the drying chamber, wherein the collector may be in the form of a filter or a sieve. A reduced pressure may have additional advantages, such as for recirculation of the atomizing gas.

In an embodiment of the present disclosure the process comprises a drying step of the formed droplets (wet particles), and wherein the water activity $(a_w)$ of the dried particles is below about 1.0, such as in the range of about 0.01 to about 0.6, such as about 0.05 to about 0.5, such as about 0.1 to about 0.5, such as about 0.2, or such as about 0.3, or such as about 0.4. Water activity $(a_w)$ is the partial vapor pressure of water in a substance divided by the standard state partial vapor pressure of water. Wherein the standard state is defined as the partial vapor pressure of pure water at the same temperature. In one embodiment of the present disclosure the water activity is chosen based on the type microorganisms, such as wherein the level of water activity is set to a value wherein said type of microorganisms is advantageously dried, such as wherein the viability is not significantly affected.

In an embodiment of the present disclosure the process comprises a drying step of the formed droplets (wet particles), and wherein the solvent (e.g. water) content of the dried particles is below about 20% by weight, such as below about 15% by weight, such as below about 10% by weight, such as below about 5% by weight, such as below about 3% by weight, such as below about 1% by weight, such as below about 0.1% by weight, with respect to the total weight of the dried particles.

In an embodiment of the present disclosure the solvent (e.g. water) content of the dried particles is below about 10% by weight, (preferably below about 5%, or below about 1% by weight), with respect to the total weight of the dried particles. Small amounts of water may consequently be present following drying of the formed droplets, and may even be advantageously, in that it may be beneficial for increased viability of the microorganisms.

Collection of Dried Particles

In an embodiment of the present disclosure the dried particles are collected at an outlet end of a drying chamber. The outlet end may further be equipped with a collector for collection of the dried particles, such as a filter, a container, and/or a sieve.

In an embodiment of the present disclosure the dried particles are collected at the outlet end of the drying chamber using a filter (such as an electrostatic filter) or a sieve. Steric interactions preferably obstructs the passage of particles, while gas, such as the atomizing gas, is allowed to pass through the collector.

In an embodiment of the present disclosure the dried particles are collected at the outlet end of the drying chamber using a sieve having an aperture diameter below about 500 micrometers, such as in the range between about 40 micrometers to about 300 micrometers, such as in the range from about 50 micrometers to about 250 micrometers, such as about 50 micrometers, such as about 100 micrometers, such as about 150 micrometers, such as about 200 micrometers or such as about 250 micrometer. Preferably the aperture diameter is below the particle size, given by Dv50, more preferably below Dv30, even more preferably below Dv10, yet even more preferably below Dv5, such as below Dv3, such as below Dv1. The apertures may be provided in a suitable shape, such as round openings and/or slits (grating). In general, the smallest dimension of an opening is the relevant size for obstruction of particles. Thereby, for slits, the aperture diameter refers to the slit width, the same reasoning applies to other shapes of openings.

In an embodiment of the present disclosure the dried particles are collected at the outlet end of the drying chamber using a sieve having an aperture diameter in the range from about 40 micrometers to about 300 micrometer.

Viability

In microbiology, a colony-forming unit (CFU, cfu, Cfu) is typically a unit used to estimate the number of viable bacteria or fungal cells in a sample. Viable is typically defined as the ability to multiply via binary fission under the controlled conditions. Counting with colony-forming units requires culturing the microbes and counts only viable cells, in contrast with microscopic examination which counts all cells, living or dead. The visual appearance of a colony in a cell culture requires significant growth, and when counting colonies it is uncertain if the colony arose from one cell or a group of cells. Expressing results as colony-forming units reflects this uncertainty. Estimation of microbial numbers by CFU may thereby undercount the number of living cells present in a sample for these reasons. This is because the counting of CFU assumes that every colony is separate and founded by a single viable microbial cell.

The most probable number method, otherwise known as the method of Poisson zeroes, is a method of getting quantitative data on concentrations of discrete items from positive/negative (incidence) data.

There are many discrete entities that are easily detected but difficult to count. Any sort of amplification reaction or catalysis reaction obliterates easy quantification but allows presence to be detected very sensitively. The MPN method involves taking the original solution or sample, and subdividing it by orders of magnitude (frequently 10× or 2×), and assessing presence/absence in multiple subdivisions.

The degree of dilution at which absence begins to appear indicates that the items have been diluted so much that there are many subsamples in which none appear. A suite of replicates at any given concentration allows for finer resolution, to use the number of positive and negative samples to estimate the original concentration within the appropriate order of magnitude.

Additionally. flow cytometry provides a rapid and reliable method to quantify viable cells in a cell suspension. One method to assess cell viability is through the use of dye exclusion. Live cells have intact membranes that exclude a variety of dyes that easily penetrate the damaged, permeable membranes of non-viable cells. Propidium iodide (PI) is a membrane impermeant dye that is generally excluded from viable cells. It binds to double stranded DNA by intercalating between base pairs. As known to a person skilled in the art, other dyes, probes and fluorescent agents are available for assessment of the viability of microorganisms by flow cytometry and/or other lab instruments such as microscopes, plate readers, cell counters and analyzers, coulter counters, haemocytometers.

As a consequence, in an embodiment of the present disclosure the dried particles include a microorganism having a viability of at least $1.0 \times 10E4$ per gram, such as defined by the most probable number (MPN), the number of colony forming units (CFU) or the number of viable cells measured by standard lab tools such as flow cytometry.

In an embodiment of the present disclosure the dried particles include a microorganism having a viability above $1.0 \times 10E4$ per gram, such as defined by the most probable number (MPN), the number of colony forming units (CFU) or the number of viable cells measured by standard lab tools such as flow cytometry, such as in the range between $1.0 \times 10E4$ to $1.0 \times 10E13$, such as in the range between about $1.0 \times 10E4$ to about $1.0 \times 10E10$ per gram, such as about $1.0 \times 10E5$, about $1 \times 10E6$, about $1.0 \times 10E7$, about $1 \times 10E8$, about $1.0 \times 10E9$, about $2.5 \times 10E9$, about $5.0 \times 10E9$, or about $7.5 \times 10E9$ per gram.

In an embodiment of the present disclosure the dried particles include a microorganism having a viability in the range between about $1.0 \times 10E4$ and about $1.0 \times 10E13$, such as about 10E6 to about 10E10, e.g. about 10E7 per gram, such as defined by the most probable number (MPN), the number of colony forming units (CFU) or the number of viable cells measured by standard lab tools such as flow cytometry.

Dried Particles

The present invention further relates to a dried particle comprising living microorganisms embedded in a mass of additive, wherein the microorganisms are not present at the surface of the particle. Preferably, the particle is compact, such that the inner void volume is below 5% of the total volume of the particle. The absence of microorganisms on the surface of the dried particles may be advantageous in that the microorganisms are embedded within the particle, and may thereby be fully surrounded by an additive, such as a drying protectant.

In an embodiment of the present disclosure the particle is not layered. Two step processes wherein a homogeneous particle comprising microorganisms and a second substance is coated by a material is preferable avoided since it adds to the complexity and may results in a decreased viability of the microorganisms during fabrication. Preferably, the particle is thereby a non-layered particle. Furthermore the dried particle is preferably a heterogeneous dried particle wherein the microorganisms and the additive and substantially not homogeneously distributed within the dried particles. In a preferred embodiment of the present disclosure the particle consists of a single phase, in addition to the microorganisms. The microorganisms may thereby be substantially embedded/surrounded by a single phase comprising an additive, such as a drying protectant. In an embodiment of the present disclosure the particle has a substantially continuous radial gradient of additive. The distribution of the additive, such as a drying protectant, within the droplets, is preferably heterogeneous with a higher concentration at the surface of the dried particles and a lower concentration at the center of the dried particles.

In an embodiment of the present disclosure the particles comprises living microorganisms. Living microorganisms are used in a wide range of areas including medicine, biotechnology, food, pharmaceutics, material industries. The industry of probiotics, for example, relies on the provision of live bacteria for stimulation of the microbiome. Furthermore, fecal microbiota transplant, has recently gained widespread recognition, wherein the microbiome of healthy donors are administered to individuals that suffer from any of the numerous microbiome related diseases. Administering may be in the digestible capsule comprising dried particles comprising a microorganism, such as bacteria. In an embodiment of the present disclosure, the microorganism is selected from the group of microorganisms normally present in the human microbiome, and may additional to bacteria include other types of microorganisms, such as archaea fungi, protists and viruses. In an embodiment of the present disclosure, the particle comprises a species of anaerobic bacteria. In an embodiment of the present disclosure the particle comprises a species of facultative anaerobic bacteria, a species of aerotolerant anaerobic bacteria, a species of obligate anaerobic bacteria, or a species of strict anaerobic bacteria, or a mixture thereof.

In an embodiment of the present disclosure the microorganism is selected from the group consisting of a facultative anaerobic bacteria, such as *Lactococcus* sp. or *Lactobacillus* sp., or a strict anaerobic bacteria, such as *Bacteroides* sp., *Faecalibacterium* sp., or *Eubacterium* sp.). Lactic acid bacteria, such as *Lactococcus* and *Lactobacillus*, are advantageously used in the food industry for industrial dairy fermentation, such as for dairy production. Furthermore, *Faecalibacterium* is one of the most abundant and important commensal bacteria of the human gut microbiota.

In an embodiment of the present disclosure the suspension comprises a gram positive bacteria selected from the list including *Eubacterium* spp., *Lactococcus* spp., *Streptococcus* spp., *Lactobacillus* spp., *Leuconostoc* spp., *Pseudoleuconostoc* spp., *Pediococcus* spp., *Brevibacterium* spp., *Enterococcus* spp., *Propionibacterium* spp., *Bifidobacterium* spp, and *Bacillus* spp. In an embodiment of the present disclosure the suspension comprises an anaerobic bacteria selected from the group consisting of *Akkermansia, Bacteroides, Bifidobacterium, Faecalibacterium, Lactobacillus,* and *Eubacterium*. In an embodiment of the present disclosure the suspension comprises a yeast. In an embodiment of the present disclosure the suspension comprises a spore forming bacteria, such as *Bacillus subtilis* sp.

In an embodiment of the present disclosure the one or more additives is selected from the group consisting of: Inositol, lactose, sucrose, trehalose, inulin, maltodextrin, dextrose, alginate or a salt thereof (e.g. sodium alginate), skimmed milk powder, yeast extract, casein peptone, hydrolyzed protein, such as hydrolyzed casein, casein or salts thereof (such as sodium caseinate), inosine, inosinemonophospate and a salt thereof, glutamine and salts thereof (such as monosodium glutaminate), ascorbic acid and salts thereof (such as sodium ascorbate), citric acid and salts thereof, polysorbate, a hydrate of Magnesium sulphate (e.g. a heptahydrate), a hydrate of Manganous sulphate (e.g. a monohydrate) and Dipotassium hydrogen phosphate, propyl gallate or a mixture thereof.

In an embodiment of the present disclosure the additive comprises a drying protectant selected from the group including cyclitols, such as inositol, and monosaccharide, such as dextrose, disaccharides such as lactose, sucrose and trehalose, polysaccharides (oligosaccharides), such as inulin, maltodextrin and starch, magnesium stearate, peptides, proteins, sugar alcohols, such as hydrogenated starch hydrolysates, fatty acid esters, alginate or a salt thereof (e.g. sodium alginate) or a mixture thereof.

In an embodiment of the present disclosure the encapsulation index, defined as the weight ratio between the microorganism and the drying protectant, is in the range between about 1:0 to about 1:10, such as in the range between about 1:1 to about 1:9, such as in the range between about 1:1 to about 1:7, such as in the range between about 1:1 to about 1:5, such as in the range between about 1:1 to about 1:3. The encapsulation index may thereby directly relate to the weight ratio between the drying protectant and the microorganisms of the formed droplet as well as that of the dried particles. While the use of drying protectant is optional, it may be preferred, depending on for example the specific type of microorganism to be dried.

In an embodiment of the present disclosure the dried particles comprises the drying protectant in the range between about 0% by weight to about 95% by weight, such as between about 50% by weight to about 90% by weight, such as between about 50% by weight to about 85% by weight, such as between about 50% by weight to about 80% by weight, such as between about 50% by weight to about 75% by weight.

In an embodiment of the present disclosure the one or more additive is selected from the group consisting of Yeast Extract, Dextrose, Polysorbate, Dipotassium hydrogen phosphate, Magnesium sulphate heptahydrate, Manganous sulphate monohydrate.

In an embodiment of the present disclosure the one or more additive is selected from the group consisting of Yeast Extract, Dextrose, Polysorbate, Dipotassium hydrogen phosphate, Magnesium sulphate heptahydrate, Manganous sulphate monohydrate and optionally a mixture of vitamins.

In an embodiment of the present disclosure the drying protectant comprises or consists of equal weights of trehalose and maltodextrin.

In an embodiment of the present disclosure the amount of emulsifier, by weight, of the suspension is below about 5%, such as below about 3%, such as below about 2%, such as below about 1%, such as about 0%, such as 0%. While emulsifier typically decreases the interfacial tension and promotes droplet formation, the use of emulsifiers at high levels can have detrimental effects to an electrostatic spray drying process, for example the emulsifiers may prevent partitioning of components of the suspension, within the formed droplets, thereby potentially leading to a decrease in the evaporation rate and the viability of the microorganisms upon drying. Furthermore, emulsifiers may affect the function and/or the viability of microorganisms. In an alternative embodiment of the present disclosure, the surfactant is a non-ionic surfactant.

In an embodiment of the present disclosure the dried particles have a size from about 1 micrometer to about 800 micrometers, such as in the range from about 5 micrometers to about 800 micrometers, such as about 10 micrometers to about 600 micrometers, such as about 10 micrometers to about 300 micrometers, such as about 10 micrometers to about 200 micrometers, such as about 10 micrometers to about 50 micrometers, or such as about 50 micrometers to about 200 micrometers, such as about 50 micrometers to about 100 micrometers, such as about 75 micrometers, or such as about 100 micrometers to about 200 micrometers, such as about 150 micrometers, measured as Dv50 values.

In an embodiment of the present disclosure the dried particles are substantially dry. Small amounts of solvent, such as trace amounts of solvent, may be present in the dried particles. Therefore in an embodiment of the present disclosure the process comprising a drying step for drying the formed droplets.

In an embodiment of the present disclosure the process comprises a drying step of the formed droplets (wet particles), and wherein the water activity $(a_w)$ of the dried particles is below about 1.0, such as in the range of about 0.01 to about 0.6, such as about 0.05 to about 0.5, such as about 0.1 to about 0.5, such as about 0.2, or such as about 0.3, or such as about 0.4. Water activity $(a_w)$ is the partial vapor pressure of water in a substance divided by the standard state partial vapor pressure of water. Wherein the standard state is defined as the partial vapor pressure of pure water at the same temperature. The water activity is preferably measured at room temperature (20-25° C.).

In one embodiment of the present disclosure the water activity is chosen based on the type microorganisms, such as wherein the level of water activity is set to a value wherein said type of microorganisms is advantageously dried, such as wherein the viability is not significantly affected.

In an embodiment of the present disclosure the process comprises a drying step of the formed droplets (wet particles), and wherein the solvent (e.g. water) content of the dried particles is below about 20% by weight, such as below about 15% by weight, such as below about 10% by weight, such as below about 5% by weight, such as below about 3% by weight, such as below about 1% by weight, such as below about 0.1% by weight, with respect to the total weight of the dried particles.

In an embodiment of the present disclosure the solvent (e.g. water) content of the dried particles is below about 10% by weight, (preferably below about 5%, or below about 1% by weight), with respect to the total weight of the dried particles. Small amounts of water may consequently be present following drying of the formed droplets, and may even be advantageously, in that it may be beneficial for increased viability of the microorganisms.

In an embodiment of the present disclosure the dried particles include a microorganism having a viability of at least 1.0×10E4 per gram, such as defined by the most probable number (MPN), the number of colony forming units (CFU) or the number of viable cells measured by standard lab tools such as flow cytometry.

In another embodiment of the present disclosure the dried particles include a microorganism having a viability above 1.0×10E4 per gram, such as defined by the most probable number (MPN), the number of colony forming units (CFU) or the number of viable cells measured by standard lab tools such as flow cytometry, such as in the range between 1.0×10E4 to 1.0×10E13, such as in the range between about 1.0×10E4 to about 1.0×10E10 per gram, such as about 1.0×10E5, about 1×10E6, about 1.0×10E7, about 1×10E8, about 1.0×10E9, about 2.5×10E9, about 5.0×10E9, or about 7.5×10E9 per gram.

In yet another embodiment of the present disclosure the dried particles include a microorganism having a viability in the range between about 1.0×10E4 and about 1.0×10E13, such as about 10E6 to about 10E10, e.g. about 10E7 per gram, such as defined by the most probable number (MPN), the number of colony forming units (CFU) or the number of viable cells measured by standard lab tools such as flow cytometry.

In an embodiment of the present disclosure the particle comprises the microorganism in the range between about 10% by weight to about 100% by weight, such as in the range between about 15% by weight to about 80% by weight, such as in the range between about 15% by weight to about 60% by weight, such as in the range between about 15% by weight to about 40% by weight, such as about 30% by weight.

In an embodiment of the present disclosure a plurality of said dried particles form a free-flowing powder, as defined in Prescott et al., On Powder Flowability, Pharmaceutical Technology, 2000.

In an embodiment of the present disclosure the dried particle is for clinical use, such as for use in and/or as medication.

In an embodiment of the present disclosure the dried particle is for consumption, such as ingestion, such as for use in/as dairy products, probiotics and/or food supplements. The dried particle may be for human and/or animal consumption.

Use of a Process

The invention further relates to use of an electrostatic spray drying process for drying of a microorganism. Preferably said process is a process for drying of a microorganism as described elsewhere herein. In an embodiment of the present disclosure the electrostatic spray drying process is defined elsewhere herein. In a preferred embodiment of the present disclosure, the use of said process is for manufacturing of dried particles, wherein the characteristics of said dried particles is as described elsewhere herein.

Items

The invention is hereinbelow described as numbered items.

1. A process for electrostatic spray drying of a living microorganism, the process comprising the following steps:
   a. Providing a suspension, comprising a number of components, including a microorganism, a solvent and an additive;
   b. Applying an electrostatic charge to said suspension;
   c. Forming droplets of said suspension, wherein the electrostatic charge has been applied such that polar components are forced towards the surface of the droplets, while less polar components are forced towards the center of the droplets;
   d. Drying said droplets, thereby forming dried particles; and
   e. (Optionally) collecting the dried particles.

2. A process for electrostatic spray drying of a living microorganism, the process comprising the following steps:
   a. Providing a suspension, comprising a number of components, including a microorganism, a solvent and an additive, wherein the suspension comprises at least 35% by weight of water;
   b. Applying an electrostatic charge to said suspension;
   c. Forming droplets of said suspension;
   d. Drying said droplets, thereby forming dried particles; and
   e. (Optionally) collecting the dried particles.

3. A process for electrostatic spray drying of a living microorganism, the process comprising the following steps:

a. Providing a suspension, comprising a number of components, including a microorganism, a solvent and an additive, wherein the microorganism is a strict anaerobic bacterium;

b. Applying an electrostatic charge to said suspension;

c. Forming droplets of said suspension;

d. Drying said droplets, thereby forming dried particles; and e. (Optionally) collecting the dried particles.

4. A process for electrostatic spray drying of a living microorganism, the process comprising the following steps:

a. Providing a suspension, comprising a number of components, including a microorganism, a solvent and an additive;

b. Applying an electrostatic charge to said suspension, wherein the electrostatic charge is applied by an electrode in contact with the suspension, and wherein the electrode has a pulsed electric potential difference;

c. Forming droplets of said suspension;

d. Drying said droplets, thereby forming dried particles; and e. (Optionally) collecting the dried particles.

5. A process for electrostatic spray drying of a living microorganism, the process comprising the following steps:

a. Providing a suspension, comprising a number of components, including a microorganism, a solvent and an additive;

b. Applying an electrostatic charge to said suspension, wherein the electrostatic charge is applied by an electrode in contact with the suspension, and wherein the electrode has an electric potential difference, with respect to ground, below about 40 kV;

c. Forming droplets of said suspension;

d. Drying said droplets, thereby forming dried particles; and e. (Optionally) collecting the dried particles.

6. A process for electrostatic spray drying of a living microorganism, the process comprising the following steps:

a. Providing a suspension, comprising a number of components, including a microorganism, a solvent and an additive;

b. Applying an electrostatic charge to said suspension;

c. Forming droplets of said suspension by the use of an atomizing gas;

d. Drying said droplets, by contacting the droplets with the atomizing gas, thereby forming dried particles; wherein the atomizing gas is heated to at least 40° C.; and e. (Optionally) collecting the dried particles.

7. The process according to any one of the preceding items, wherein the electrostatic charge is applied to the suspension by contacting said suspension with at least one electrode having an electric potential difference with respect to ground.

8. The process according to any one of the preceding items, wherein the electrode has an electric potential difference, with respect to ground, below about 40 kV, such as below about 35 kV, such as below about 30 kV, such as below about 25 kV, such as below about 20 kV, such as below about 15 kV, such as below about 10 kV.

9. The process according to any one of the preceding items, wherein the electrode, has a fixed polarity, with respect to ground, such as fixed negative polarity or fixed positive polarity.

10. The process according to any one of the preceding items, wherein the electric potential difference, with respect to ground, of the electrode varies over time, such as in periodic variations.

11. The process according to any one of the preceding items, wherein the electric potential difference, with respect to ground, of the electrode varies periodically, such as in a periodic step function.

12. The process according to any one of the preceding items, wherein the electric potential of the electrode is applied by pulse width modulation, such as by a square wave.

13. The process according to any one of the preceding items, wherein components of the suspension are partitioned within the formed droplets with respect to their polarity, such as for increased evaporation of the solvent and/or increased encapsulation of the microorganism.

14. The process according to any one of the preceding items, wherein components of the suspension of higher polarity are partitioned to the surface of the droplets and components of the suspension of lower polarity are partitioned to the center of the droplets.

15. The process according to any one of the preceding items, wherein at least two components of said suspension have different dielectric properties.

16. The process according to any one of the preceding items, wherein the microorganism has a lower effective dielectric property than the additive and/or the solvent.

17. The process according to any one of the preceding items, wherein the solvent has a higher dielectric constant than the additive, and the additive has a higher dielectric constant than the microorganism.

18. The process according to any one of the preceding items, wherein the suspension comprises living microorganisms.

19. The process according to any one of the preceding items, wherein the suspension comprises a species of facultative anaerobic bacteria or a species of strict anaerobic bacteria.

20. The process according to any one of the preceding items, wherein the suspension comprises a species of strict anaerobic bacteria.

21. The process according to any one of the preceding items, wherein the microorganism is selected from the group consisting of a facultative anaerobic bacteria such as *Lactococcus* sp. or *Lactobacillus* sp., or a strict anaerobic bacteria, such as *Faecalibacterium* sp., or *Eubacterium* sp.).

22. The process according to any one of the preceding items, wherein the suspension comprises at least one species of strict anaerobic bacteria selected from the group consisting of *Adlercreutzia* sp., *Akkermansia* sp., *Alistipes* sp., *Anaerotruncus* sp., *Bacteroidales, Bacteroides* sp., *Blautia* sp., *Butyricicoccus* sp., *Butyrivibrio* sp., *Catabacteriaceae* sp., *Christensenella* sp., *Clostridiales* sp., *Clostridium* sp., *Collinsella* sp., *Coprococcus* sp., *Cutibacterium* sp., *Dialister* sp., *Dorea* sp., *Erysipelotrichaceae* sp. *Eubacterium* sp., *Faecalibacterium* sp., *Flavonifractor* sp., *Fusobacterium* sp., *Hafnia* sp., *Holdemania* sp., *Hungatella* sp., *Intestinibacter* sp., *Lachnobacterium* sp., *Lachnospira* sp., *Lachnospiraceae* sp, *Lachnospiraceae gen. nov.* sp. *nov, Lachnospiraceae* sp. *nov., Methanobrevibacter* sp., *Methanomassiliicoccus* sp., *Methanosarcina* sp., *Mitsuokella* sp., *Odoribacter* sp., *Oscillospira* sp., *Oxalobacter* sp., *Parabacteroides* sp., *Phascolarctobacterium* sp., *Porphyromonadaceae* sp., *Prevotella* sp., *Propionibacterium* sp., *Rikenellaceae* sp., *Roseburia* sp., *Ruminococcus* sp., *Subdoligranulum* sp., *Sutterella* sp., *Turicibacteraceae* sp.

23. The process according to any one of the preceding items, wherein the suspension comprises at least one species of strict anaerobic bacteria selected from the group consisting of *Adlercreutzia* sp., *Adlercreutzia equolifaciens, Akkermansia* sp., *Akkermansia muciniphila, Alistipes* sp., *Alistipes finegoldii, Alistipes hadrus, Alistipes indistinctii, Alistipes onkerdonkii, Alistipes putredinis Alistipes shahii, Anaerostipes* sp. *Anaerostipes caccae, Anaerostipes hadrus, Anaerotruncus* sp., *Bacteroidales, Bacteroides* sp., *Bacteroides dorei, Bacteroides fragilis, Bacteroides intestinalis, Bacteroides intestinihominis, Bacteroides ovatus, Bacteroides putredinis, Bacteroides thetaiotaomicron, Bacteroides uniformis, Bacteroides vulgatus, Bacteroides xylanisolvens, Blautia* sp*, Blautia luti, Blautia obeum, Blautia wexlerae, Butyricicoccus, Butyrivibrio fibrisolvens, Butyrivibrio* sp., *Catabacteriaceae, Christensenella* sp., *Clostridiales, Clostridium* sp., *Clostridium scindens, Clostridium spiroforme, Clostridium butyricum, Collinsella* sp., *Collinsella aerofaciens, Coprococcus* sp., *Coprococcus catus, Coprococcus comes, Coprococcus eutactus, Coprococcus* sp., *Cutibacterium acnes, Dialister* sp., *Dialister invisus, Dorea* sp., *Dorea formicigenerans, Dorea longicatena, Erysipelotrichaceae, Eubacterium* sp. *Eubacterium eligens, Eubacterium hallii, Eubacterium limosum, Eubacterium ramulus, Eubacterium rectale, Eubacterium siraeum, Eubacterium ventriosum, Faecalibacterium* sp., *Faecalibacterium prausnitzii, Flavonifractor plautii, Fusobacterium prausnitzii, Hafnia, Holdemania, Hungatella hathewayi, Intestinibacter bartlettii, Lachnobacterium, Lachnospira, Lachnospira pectinoshiza, Lachnospiraceae, Lachnospiraceae gen. nov.* sp. *nov, Lachnospiraceae* sp. *nov., Methanobrevibacter* sp., *Methanomassiliicoccus* sp., *Methanosarcina, Mitsuokella multiacidus, Odoribacter, Oscillospira, Oxalobacter formigenes, Parabacteroides* sp., *Parabacteroides distasonis, Phascolarctobacterium, Porphyromonadaceae, Prevotella* sp., *Prevotella albensis, Prevotella amnii, Prevotella bergensis, Prevotella bivia, Prevotella brevis, Prevotella bryantii, Prevotella buccae, Prevotella buccalis, Prevotella copri, Prevotella dentalis, Prevotella denticola, Prevotella disiens, Prevotella histicola, Prevotella intermedia, Prevotella maculosa, Prevotella marshii, Prevotella melaninogenica, Prevotella micans, Prevotella multiformis, Prevotella nigrescens, Prevotella oralis, Prevotella oris, Prevotella oulorum, Prevotella pallens, Prevotella salivae, Prevotella stercorea, Prevotella tannerae, Prevotella timonensis, Prevotella veroralis, Propionibacterium acnes, Rikenellaceae, Roseburia* sp. *Roseburia faecis, Roseburia hominis, Roseburia intestinalis, Roseburia inulinivorans, Ruminococcus* sp., *Ruminococcus bicirculans, Ruminococcus gauvreauii, Ruminococcus gnavus, Ruminococcus lactaris, Ruminococcus obeum, Ruminococcus torques, Ruminococcus albus, Ruminococcus bromii, Ruminococcus callidus, Ruminococcus flavefa-ciens, Ruminococcus gauvreauii, Subdoligranulum, Sutterella* and *Turicibacteraceae.*

24. The process according to any one of the preceding items, wherein the suspension comprises an anaerobic bacteria selected from the group consisting of *Bifidobacterium, Faecalibacterium, Lactobacillus, Eubacterium.*

25. The process according to any one of the preceding items, wherein the suspension comprises a gram positive bacteria selected from the list including *Lactococcus* spp., *Streptococcus* spp., *Lactobacillus* spp., *Leuconostoc* spp., *Pseudoleuconostoc* spp., *Pediococcus* spp., *Brevibacterium* spp., *Enterococcus* spp., *Propionibacterium* spp., *Bifidobacterium* spp, *Bacillus* spp.

26. The process according to any one of the preceding items, wherein the suspension comprises a yeast.

27. The process according to any one of the preceding items, wherein the suspension comprises a spore forming bacterium, such as *Bacillus subtilis* sp.

28. The process according to any one of the preceding items, wherein the droplets are formed by spraying the suspension.

29. The process according to any one of the preceding items, wherein the formation of droplets is carried out by means of an atomizing device, such as an ultrasound nozzle; a pressure nozzle; a two-fluid nozzle (e.g. using a gas such as CO2 or N2 as atomizing gas); a vibrating nozzle; a frequency nozzle, an electrostatic nozzle; or a rotating atomizing device.

30. The process according to any one of the preceding items, wherein the formation of droplets is carried out by means of a two-fluid nozzle.

31. The process according to any one of the preceding items, wherein the formation of droplets in step c) is performed using an atomizing gas.

32. The process according to any one of the preceding items, wherein the atomizing gas is selected from the group consisting of an inert gas (such as Nitrogen and Carbon dioxide), a noble gas (e.g. Helium, Argon or Neon), and an alkane gas (such methane), or a mixture thereof.

33. The process according to any one of the preceding items, wherein the atomizing gas comprises or consists of Nitrogen, Carbon Dioxide and/or atmospheric gas.

34. The process according to any one of the preceding items, wherein the atomizing gas has not been dehumidified.

35. The process according to any one of the preceding items, wherein the atomizing gas has a moisture content below about 1000 ppm, such as below about 500 ppm, such as about below 100 ppm, such as about below 50 ppm, such as about below 10 ppm.

36. The process according to any one of the preceding items, wherein the droplet forming step, (e.g. the spray step) is carried out with an atomizing gas inlet temperature of at most about 200° C., such as in the range between about 20° C. to about 200° C., such as in the range between about 40° C. to about 150° C., or such as in the range between about 40° C. to about 120° C., such as between about 40° C. to about 90° C., such as between about 50° C. to about 90° C., such as between about 60° C. to about 85° C., such as about 80° C.

37. The process according to any one of the preceding items, wherein the atomizing gas has an inlet pressure in the range between about 1 kPa to about 500 kPa, such as in the range between about 5 kPa to about 500 kPa, such as in the range between about 5 kPa to about 300 kPa, such as in the range between about 5 kPa to about 100 kPa, such as about 60 kPa, or such as about 70 kPa, or such as about 80 kPa, or such as in the range between about 100 kPa to about 400 kPa, such as about 120 kPa, or about 150 kPa, or about 200 kPa, or about 250 kPa, or about 300 kPa, or about 350 kPa.

38. The process according to any one of the preceding items, wherein the atomizing gas has an inlet pressure in the range between about 50 kPa to about 400 kPa.

39. The process according to any one of the preceding items, wherein the suspension has a viscosity in the range between about 1 mPa·s to about 10,000 mPa·s, such as in the range between about 10 mPa·s to about 5,000 mPa·s, such as in the range between about 50 mPa·s to about 5,000 mPa·s, such as in the range between about 50 mPa·s to about 3,000 mPa·s, such as in the range between about 50 mPa·s to about 1,000 mPa·s, such as in the range between about 50 mPa·s to about 500 mPa·s, such as in the range between about 70 mPa·s to about 300 mPa·s, such as about 100 mPa·s.

40. The process according to any one of the preceding items, wherein the solvent comprises or consists of water.

41. The process according to any one of the preceding items, wherein the suspension comprises at least 35% by weight water, such as at least 40% by weight water, such as at least 50% by weight water, such as at least 60% by weight water, such as at least 70% by weight water, for example at least 80% by weight water, such as at least 90% by weight water, for example up to 95% by weight water.

42. The process according to any one of the preceding items, wherein the suspension comprises the additive in the range between about 5% by weight to about 60% by weight, such as in the range between about 5% by weight to about 50% by weight, such as in the range between about 5% by weight to about 40% by weight, such as in the range between about 5% by weight to about 30% by weight, such as in the range between about 5% by weight to about 20% by weight, such as about 10% by weight.

43. The process according to any one of the preceding items, wherein the suspension comprises the microorganism in the range between about 10% by weight to about 60% by weight, such as in the range between about 15% by weight to about 50% by weight, such as in the range between about 15% by weight to about 40% by weight, such as in the range between about 15% by weight to about 30% by weight, such as about 20% by weight.

44. The process according to any one of the preceding items, wherein the droplets are dried in a drying chamber and wherein the major accelerating force(s), for movement of the droplets through the drying chamber, is gravity and/or forces due to interactions with the spray gas, such as drag force.

45. The process according to any one of the preceding items, wherein the droplets are dried in a drying chamber and wherein the major accelerating force(s), for movement of the droplets through the drying chamber, is not due to electrostatic interactions with electric fields.

46. The process according to any one of the preceding items, wherein the movement of droplets through the drying chamber is substantially not due to interaction with an electrical field.

47. The process according to any one of the preceding items, wherein the suspension comprises one or more additives, such as a stabilizing additive.

48. The process according to any one of the preceding items, wherein one or more additives are added to the suspension prior to step c), such as prior to step b) or step a).

49. The process according to any one of the preceding items, wherein the one or more additives is selected from the group consisting of: Inositol, lactose, sucrose, trehalose, inulin, maltodextrin, dextrose, alginate or a salt thereof (e.g. sodium alginate), skimmed milk powder, yeast extract, casein peptone, hydrolyzed protein, such as hydrolyzed casein, casein or salts thereof (such as sodium caseinate), inosine, inosinemonophospate and a salt thereof, glutamine and salts thereof (such as monosodium glutaminate), ascorbic acid and salts thereof (such as sodium ascorbate), citric acid and salts thereof, polysorbate, a hydrate of Magnesium sulphate (e.g. a heptahydrate), a hydrate of Manganous sulphate (e.g. a monohydrate) and Dipotassium hydrogen phosphate, propyl gallate or a mixture thereof.

50. The process according to any one of the preceding items, wherein the additive comprises a drying protectant selected from the group including cyclitols, such as inositol, and monosaccharide, such as dextrose, disaccharides such as lactose, sucrose and trehalose, polysaccharides (oligosaccharides), such as inulin, maltodextrin and starch, magnesium stearate, peptides, proteins, sugar alcohols, such as mannitol, sorbitol, or hydrogenated starch hydrolysates, fatty acid esters, alginate or a salt thereof (e.g. sodium alginate) or a mixture thereof.

51. The process according to any one of the preceding items, wherein the encapsulation index, defined as the weight ratio between the microorganism and the drying protectant, is in the range between about 1:0 to about 1:10, such as in the range between about 1:1 to about 1:9, such as in the range between about 1:1 to about 1:7, such as in the range between about 1:1 to about 1:5, such as in the range between about 1:1 to about 1:3.

52. The process according to any one of the preceding items, wherein the dried particle comprises the drying protectant in the range between about 0% by weight to about 95% by weight, such as between about 50% by weight to about 90% by weight, such as between about 50% by weight to about 85% by weight, such as between about 50% by weight to about 80% by weight, such as between about 50% by weight to about 75% by weight.

53. The process according to any one of the preceding items, wherein the one or more additive is selected from the group consisting of Yeast Extract, Dextrose, Polysorbate, Dipotassium hydrogen phosphate, Magnesium sulphate heptahydrate, Manganous sulphate monohydrate.

54. The process according to any one of the preceding items, wherein the one or more additive is selected from the group consisting of Yeast Extract, Dextrose, Polysorbate, Dipotassium hydrogen phosphate, Magnesium sulphate heptahydrate, Manganous sulphate monohydrate and optionally a mixture of vitamins.

55. The process according to any one of the preceding items, wherein the drying protectant comprises or consists of equal weights of trehalose and maltodextrin.

56. The process according to any one of the preceding items, wherein the amount of emulsifier, by weight, of the suspension is below about 5%, such as below about 3%, such as below about 2%, such as below about 1%, such as about 0%, such as 0%.

57. The process according to any one of the preceding items, wherein the microorganism is an anaerobic bacteria and all steps, from cultivation to collection of dried particles, are carried out in the presence of less than about 5% oxygen, such as less than about 2% oxygen, preferably less than about 1% oxygen, such as 0.5% oxygen, such as less than about 0.05% oxygen.

58. The process according to any one of the preceding items, wherein the microorganism is an anaerobic bacteria and all steps, from cultivation to collection of dried particles, are carried out in the presence of less than about 0.5% oxygen, such as less than about 0.25% oxygen, such as less than about 0.1% oxygen, such as less than about 0.05% (about 5 ppm) oxygen, such as less than about 0.02% oxygen, or less than about 0.03% oxygen, or less than about 0.04% oxygen.

59. The process according to any one of the preceding items, wherein the microorganism is an anaerobic bacteria and all steps, from cultivation to collection of dried particles, are carried out in the presence of oxygen in the range between about 0.0001% to about 2% oxygen, such as in the range of about 0.0001% to about 0.5% oxygen, such as in the range between about 0.001% to about 0.05% oxygen, e.g. in the range between about 0.001% to about 0.025% oxygen, such as about 0.01% oxygen, or such as about 0.02% oxygen, or in the range between about 0.025% to about 0.05% oxygen, such as about 0.03% oxygen, or such as about 0.04% oxygen.

60. The process according to any one of the preceding items, wherein the microorganism is an anaerobic bacteria and all steps, from cultivation to collection of dried particles, are carried out under essentially anaerobic conditions.

61. The process according to any one of the preceding items, further comprising a concentrating step prior to step b), such as prior to step a).

62. The process according to any one of the preceding items, further comprising a fermentation step prior to step b), such as prior to step a.

63. The process according to any one of the proceedings items, further comprising a washing step prior to step b, such as prior to step a), wherein a suspension of microorganisms (e.g. bacteria) is washed to remove components from the suspension of microorganism, e.g. components of the culture medium.

64. The process according to any one of the preceding items, comprising a fermentation step, a concentration step, and the process steps a) to b), or process steps a) to c), or process steps a) to d), or process steps a) to e), which are all performed in the presence of no more than 0.5% oxygen, such as less than 0.05% oxygen.

65. The process according to any one of the preceding items, comprising a fermentation step, a concentration step, and the process steps a) to b), or process steps a) to c), or process steps a) to d), or process steps a) to e), which are all performed under essentially anaerobic conditions.

66. The process according to any one of the preceding items, comprising a fermentation step, concentration step, a washing step, and the process steps a) to b), or process steps a) to c), or process steps a) to d), or process steps a) to e), which are all performed in the presence of no more than 0.5% oxygen, such as less than 0.05% oxygen.

67. The process according to any one of the preceding items, comprising a fermentation step, concentration step, a washing step, and the process steps a) to b), or process steps a) to c), or process steps a) to d), or process steps a) to e), which are all performed under essentially anaerobic conditions.

68. The process according to any one of the preceding items, wherein the dried particles have a size from about 1 micrometer to about 800 micrometers, such as in the range from about 5 micrometers to about 800 micrometers, such as about 10 micrometers to about 600 micrometers, such as about 10 micrometers to about 300 micrometers, such as about 10 micrometers to about 200 micrometers, such as about 10 micrometers to about 50 micrometers, or such as about 50 micrometers to about 200 micrometers, such as about 50 micrometers to about 100 micrometers, such as about 75 micrometers, or such as about 100 micrometers to about 200 micrometers, such as about 150 micrometers, measured as Dv50 values.

69. The process according to any one of the preceding items, wherein the size distribution of the dried particles is substantially unimodal.

70. The process according to any one of the preceding items, wherein the dried particles are substantially dry.

71. The process according to any one of the preceding items, the process comprising a drying step for drying the formed droplets.

72. The process according to any one of the preceding items, the process comprising a drying step, and wherein the drying of the droplets takes place under reduced pressure.

73. The process according to any one of the preceding items, wherein the process comprises a drying step of the formed droplets (wet particles), and wherein the water activity ($a_w$) of the dried particles is below about 1.0, such as in the range of about 0.01 to about 0.6, such as about 0.05 to about 0.5, such as about 0.1 to about 0.5, such as about 0.2, or such as about 0.3, or such as about 0.4.

74. The process according to any one of the preceding items, wherein the process comprises a drying step of the formed droplets (wet particles), and wherein the solvent (e.g. water) content of the dried particles is below about 20% by weight, such as below about 15% by weight, such as below about 10% by weight, such as below about 5% by weight, such as below about 3% by weight, such as below about 1% by weight, such as below about 0.1% by weight, with respect to the total weight of the dried particles.

75. The process according to any one of the preceding items, wherein the solvent (e.g. water) content of the dried particles is below about 10% by weight, (preferably below about 5%, or below about 1% by weight), with respect to the total weight of the dried particles.

76. The process according to any one of the preceding items, wherein the dried particles are collected at an outlet end of a drying chamber.

77. The process according to any one of the preceding items, wherein the dried particles are collected at the outlet end of the drying chamber using a filter (such as an electrostatic filter) or a sieve.

78. The process according to any one of the preceding items, wherein the dried particles are collected at the outlet end of the drying chamber using a sieve having an aperture diameter below about 500 micrometers, such as in the range between about 40 micrometers to about 300 micrometers, such as in the range from about 50 micrometers to about 250 micrometers, such as about 50 micrometers, such as about 100 micrometers, such as about 150 micrometers, such as about 200 micrometers or such as about 250 micrometer.

79. The process according to any one of the preceding items, wherein the dried particles are collected at the outlet end of the drying chamber using a sieve having an aperture diameter in the range from about 40 micrometers to about 300 micrometer.

80. The process according to any one of the preceding items, wherein the dried particles include a microorganism having a viability of at least 1.0×10E4 per gram, such as defined by the most probable number (MPN), the number of colony forming units (CFU) or the number of viable cells as measured by standard lab tools such as flow cytometry.

81. The process according to any one of the preceding items, wherein the dried particles include a microorganism having a viability in the range between about 1.0×10E4 and 1.0×10E13 per gram, such as defined by the most probable number (MPN), the number of colony forming units (CFU) or the number of viable cells measured by standard lab tools such as flow cytometry, such as about 1.0×10E5.

82. The process according to any one of the preceding items, wherein the dried particles include a microorganism having a viability of at least 1.0×10E4 per gram, such as defined by the most probable number (MPN), the number of colony forming units (CFU) or the number of viable cells measured by standard lab tools such as flow cytometry.

83. The process according to any one of the preceding items, wherein the dried particles include a microorganism having a viability above 1.0×10E4 per gram, such as defined by the most probable number (MPN), the number of colony forming units (CFU) or the number of viable cells measured by standard lab tools such as flow cytometry, such as in the range between 1.0×10E4 to 1.0×10E13, such as in the range between about 1.0×10E4 to about 1.0×10E10 per gram, such as about 1.0×10E5, about 1×10E6, about 1.0×10E7, about 1×10E8, about 1.0×10E9, about 2.5×10E9, about 5.0×10E9, or about 7.5×10E9 per gram, such as defined by the most probable number (MPN), the number of colony forming units (CFU) or the number of viable cells measured by standard lab tools such as flow cytometry.

84. The process according to any one of the preceding items, wherein the dried particles include a microorganism having a viability in the range between about 1.0×10E4 and about 1.0×10E13, such as about 10E6 to about 10E10, e.g. about 10E7 per gram, such as defined by the most probable number (MPN), the number of colony forming units (CFU) or the number of viable cells measured by standard lab tools such as flow cytometry.

85. A dried particle comprising living microorganisms embedded in a mass of additive wherein the microorganisms are not present at the surface of the particle.

86. The particle according to item 85, wherein the particle is not layered, such as wherein the particle has a substantially continuous radial gradient of additive.

87. The particle according to items 85 to 86, wherein the particle has a total inner void volume below 5% of the total volume of the particle.

88. The particle according to items 85 to 87, wherein the particles comprises living microorganisms.

89. The particle according to items 85 to 88, wherein the microorganism is selected from the group consisting of a facultative anaerobic bacteria, such as *Lactococcus* sp. or *Lactobacillus* sp., or a strict anaerobic bacteria, such as *Faecalibacterium* sp., or *Eubacterium* sp.).

90. The particle according to items 85 to 89, wherein the suspension comprises a gram positive bacteria selected from the list including *Lactococcus* spp., *Streptococcus* spp., *Lactobacillus* spp., *Leuconostoc* spp., *Pseudoleuconostoc* spp., *Pediococcus* spp., *Brevibacterium* spp., *Enterococcus* spp., *Propionibacterium* spp., *Bifidobacterium* spp, *Bacillus* spp.

91. The particle according to items 85 to 90, wherein the suspension comprises an anaerobic bacteria selected from the group consisting of *Bifidobacterium, Faecalibacterium, Lactobacillus, Eubacterium*.

92. The particle according to items 85 to 91, wherein the suspension comprises a yeast.

93. The particle according to items 85 to 92, wherein the suspension comprises a spore forming bacteria, such as *Bacillus subtilis* sp.

94. The particle according to items 85 to 93, wherein the one or more additives is selected from the group consisting of: Inositol, lactose, sucrose, trehalose, inulin, maltodextrin, dextrose, alginate or a salt thereof (e.g. sodium alginate), skimmed milk powder, yeast extract, casein peptone, hydrolyzed protein, such as hydrolyzed casein, casein or salts thereof (such as sodium caseinate), inosine, inosinemonophospate and a salt thereof, glutamine and salts thereof (such as monosodium glutaminate), ascorbic acid and salts thereof (such as sodium ascorbate), citric acid and salts thereof, polysorbate, a hydrate of Magnesium sulphate (e.g. a heptahydrate), a hydrate of Manganous sulphate (e.g. a monohydrate) and Dipotassium hydrogen phosphate, propyl gallate or a mixture thereof.

95. The particle according to items 85 to 94, wherein the additive comprises a drying protectant selected from the group including cyclitols, such as inositol, and monosaccharide, such as dextrose, disaccharides such as lactose, sucrose and trehalose, polysaccharides (oligosaccharides), such as inulin, maltodextrin and starch, magnesium stearate, peptides, proteins, sugar alcohols, such as hydrogenated starch hydrolysates, fatty acid esters, alginate or a salt thereof (e.g. sodium alginate) or a mixture thereof.

96. The particle according to items 85 to 95, wherein the encapsulation index, defined as the weight ratio between the microorganism and the drying protectant, is in the range between about 1:0 to about 1:10, such as in the range between about 1:1 to about 1:9, such as in the range between about 1:1 to about 1:7, such as in the range between about 1:1 to about 1:5, such as in the range between about 1:1 to about 1:3.

97. The particle according to items 85 to 96, wherein the dried particle comprises the drying protectant in the range between about 0% by weight to about 95% by weight, such as between about 50% by weight to about 90% by weight, such as between about 50% by weight to about 85% by weight, such as between about 50% by weight to about 80% by weight, such as between about 50% by weight to about 75% by weight.

98. The particle according to items 85 to 97, wherein the one or more additive is selected from the group consisting of Yeast Extract, Dextrose, Polysorbate, Dipotassium hydrogen phosphate, Magnesium sulphate heptahydrate, Manganous sulphate monohydrate.

99. The particle according to items 85 to 98, wherein the one or more additive is selected from the group consisting of Yeast Extract, Dextrose, Polysorbate, Dipotassium hydrogen phosphate, Magnesium sulphate heptahydrate, Manganous sulphate monohydrate and optionally a mixture of vitamins.

100. The particle according to items 85 to 99, wherein the drying protectant comprises or consists of equal weights of trehalose and maltodextrin.

101. The particle according to items 85 to 100, wherein the amount of emulsifier, by weight, of the suspension is below about 5%, such as below about 3%, such as below about 2%, such as below about 1%, such as about 0%, such as 0%.

102. The particle according to items 85 to 101, wherein the dried particles have a size from about 1 micrometer to about 800 micrometers, such as in the range from about 5 micrometers to about 800 micrometers, such as about 10 micrometers to about 600 micrometers, such as about 10 micrometers to about 300 micrometers, such as about 10 micrometers to about 200 micrometers, such as about 10 micrometers to about 50 micrometers, or such as about 50 micrometers to about 200 micrometers, such as about 50 micrometers to about 100 micrometers, such as about 75 micrometers, or such as about 100 micrometers to about 200 micrometers, such as about 150 micrometers, measured as Dv50 values.

103. The particle according to items 85 to 102, wherein the dried particles are substantially dry.

104. The particle according to items 85 to 103, wherein the process comprises a drying step of the formed droplets (wet particles), and wherein the water activity ($a_w$) of the dried particles is below about 1.0, such as in the range of about 0.01 to about 0.6, such as about 0.05 to about 0.5, such as about 0.1 to about 0.5, such as about 0.2, or such as about 0.3, or such as about 0.4.

105. The particle according to items 85 to 104, wherein the process comprises a drying step of the formed droplets (wet particles), and wherein the solvent (e.g. water) content of the dried particles is below about 20% by weight, such as below about 15% by weight, such as below about 10% by weight, such as below about 5% by weight, such as below about 3% by weight, such as below about 1% by weight, such as below about 0.1% by weight, with respect to the total weight of the dried particles.

106. The particle according to items 85 to 105, wherein the solvent (e.g. water) content of the dried particles is below about 10% by weight, (preferably below about 5%, or below about 1% by weight), with respect to the total weight of the dried particles.

107. The particle according to items 85 to 106, wherein the dried particles include a microorganism having a viability of at least $1.0 \times 10E4$ per gram, such as defined by the most probable number (MPN), the number of colony forming units (CFU) or the number of viable cells measured by standard lab tools such as flow cytometry.

108. The particle according to items 85 to 107, wherein the dried particles include a microorganism having a viability in the range between about $1.0 \times 10E4$ and $1.0 \times 10E13$ per gram of dry particle mass, such as defined by the most probable number (MPN), the number of colony forming units (CFU) or the number of viable cells measured by standard lab tools such as flow cytometry, such as about $1.0 \times 10E5$.

109. The particle according to items 85 to 108, wherein the dried particles include a microorganism having a viability of at least $1.0 \times 10E4$ per gram, such as defined by the most probable number (MPN), the number of colony forming units (CFU) or the number of viable cells measured by standard lab tools such as flow cytometry.

110. The particle according to items 85 to 109, wherein the dried particles include a microorganism having a viability above $1.0 \times 10E4$ per gram, such as defined by the most probable number (MPN), the number of colony forming units (CFU) or the number of viable cells measured by standard lab tools such as flow cytometry, such as in the range between $1.0 \times 10E4$ to $1.0 \times 10E13$, such as in the range between about $1.0 \times 10E4$ to about $1.0 \times 10E10$ per gram, such as about $1.0 \times 10E5$, about $1 \times 10E6$, about $1.0 \times 10E7$, about $1 \times 10E8$, about $1.0 \times 10E9$, about $2.5 \times 10E9$, about $5.0 \times 10E9$, or about $7.5 \times 10E9$ per gram, such as defined by the most probable number (MPN), the number of colony forming units (CFU) or the number of viable cells measured by standard lab tools such as flow cytometry.

111. The particle according to items 85 to 110, wherein the dried particles include a microorganism having a viability in the range between about $1.0 \times 10E4$ and about $1.0 \times 10E13$, such as about 10E6 to about 10E10, e.g. about 10E7 per gram, such as defined by the most probable number (MPN), the number of colony forming units (CFU) or the number of viable cells measured by standard lab tools such as flow cytometry.

112. The particle according to items 85 to 111, wherein the particle comprises the microorganism in the range between about 10% by weight to about 100% by weight, such as in the range between about 15% by weight to about 80% by weight, such as in the range between about 15% by weight to about 60% by weight, such as in the range between about 15% by weight to about 40% by weight, such as about 30% by weight.

113. The particle according to items 85 to 112, wherein a plurality of said dried particles form a free-flowing powder.

114. The particle according to items 85 to 113, wherein the dried particle is for clinical use.

115. The particle according to items 85 to 114, wherein the dried particle is for consumables, such as for use in a dairy product.

116. Use of an electrostatic spray drying process for drying of a microorganism.

117. The use according to items 116, wherein the electrostatic spray drying process is defined by items 1-84.

118. The use according to items 116-117 wherein the use results in a particle as defined by items 85-115.

DETAILED DESCRIPTION OF DRAWINGS

The invention will in the following be described in greater detail with reference to the accompanying drawings. The drawings are exemplary and are intended to illustrate some of the features of the presently disclosed methods for electrostatic spray drying of microorganisms and microorganisms embedded in dried particles, and are not to be construed as limiting to the presently disclosed invention.

Figure 5A:
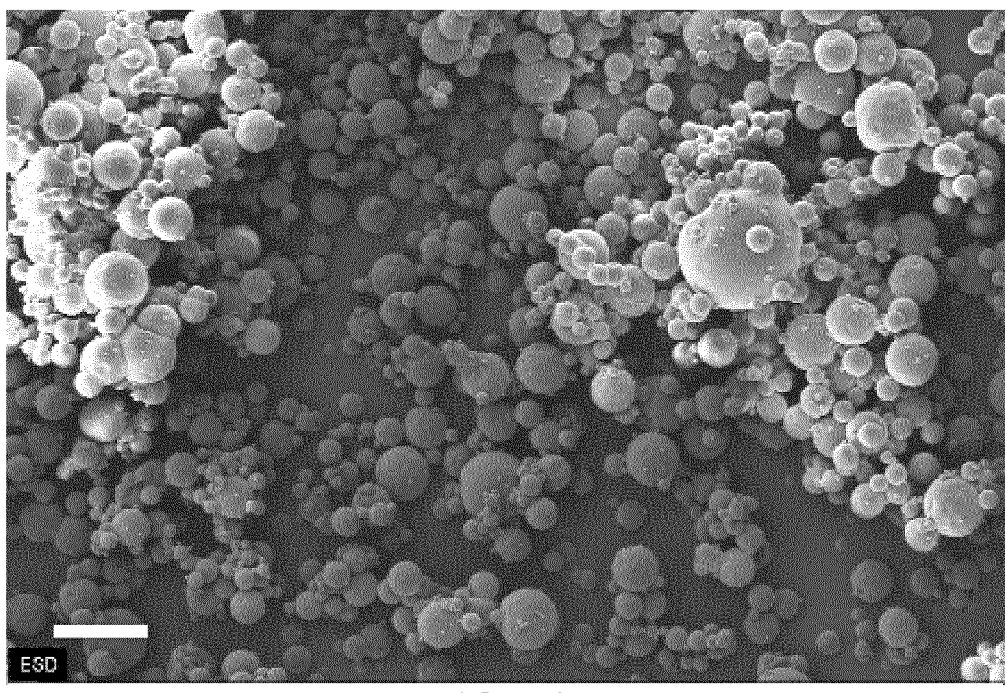
Figure 5B:
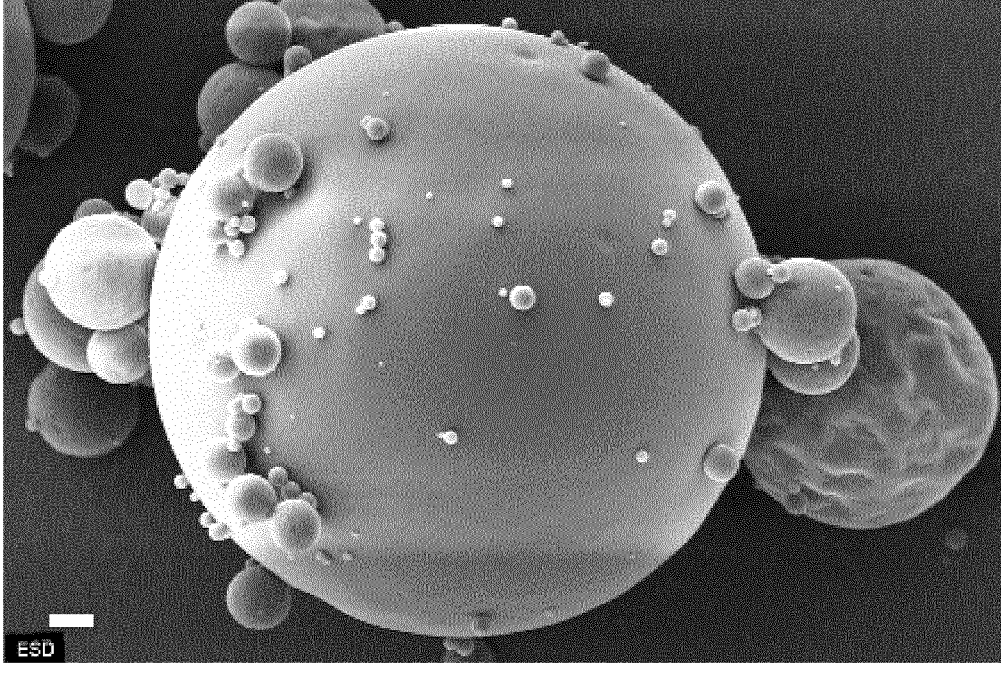

FIG. 5A-B show scanning electron micrographs of electrostatically spray dried particles comprising an additive and *Lactobacillus rhamnosus* microorganisms at different magnifications.

Figure 6A:
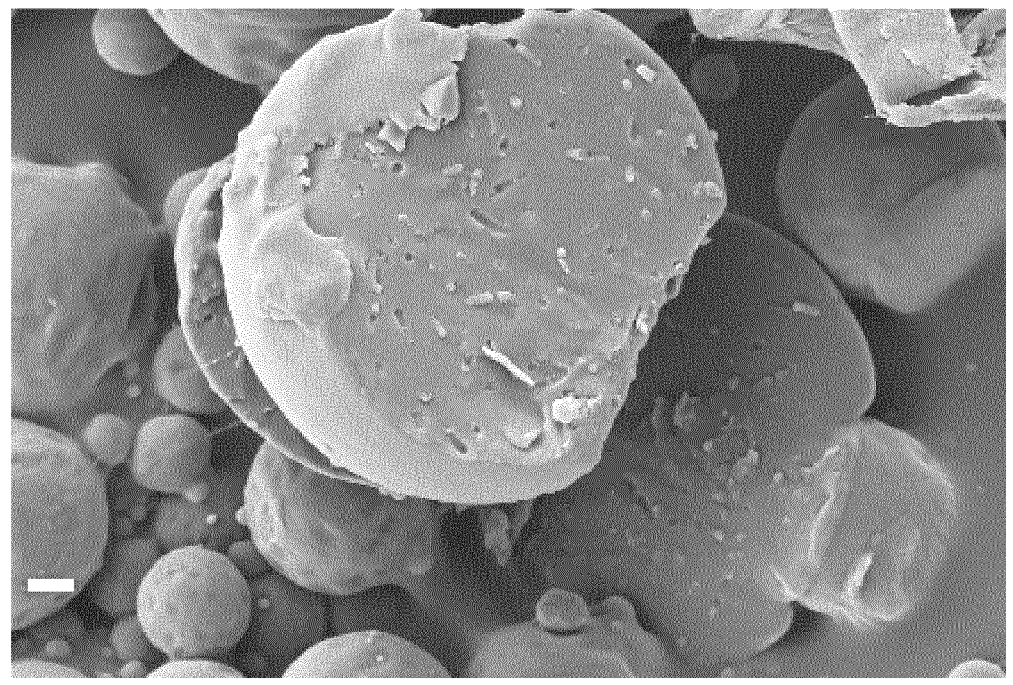
Figure 6B:
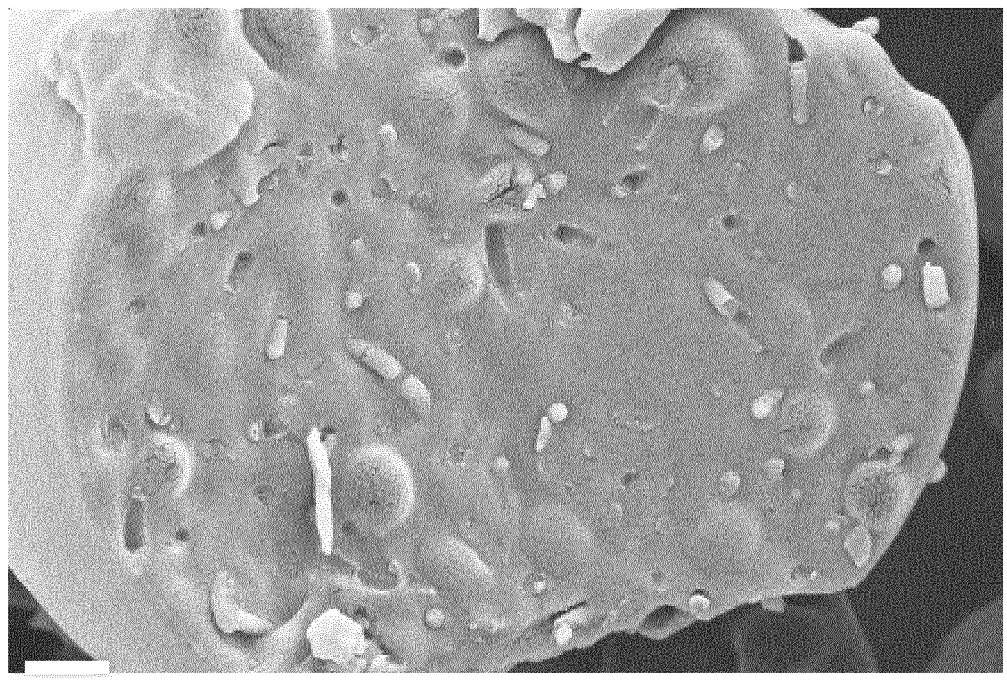

FIG. 6A-B show scanning electron micrographs of cross sections of dried particles shown in FIG. 5. The dried particles comprise an additive and microorganisms.

FIG. 7 A-C show scanning electron micrographs of cross sections of electrostatically spray dried particles of the invention. The dried particles comprise an additive and microorganisms, *B. breve*.

Figure 8A:
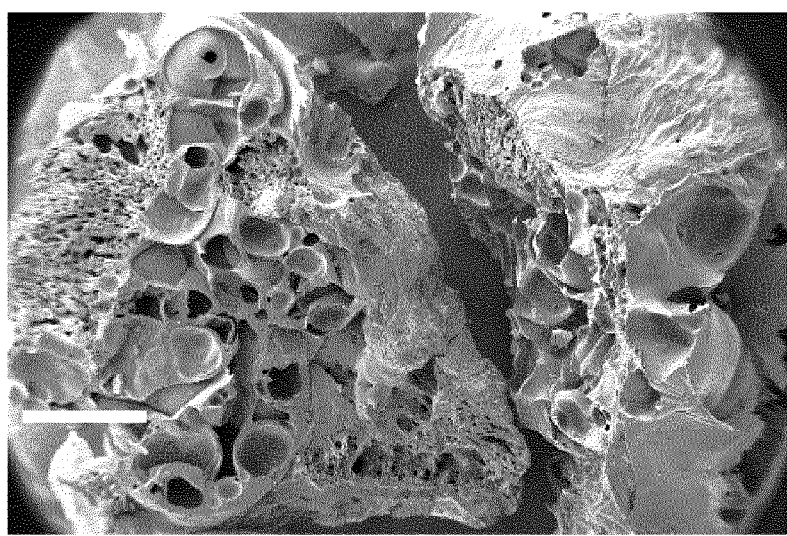
Figure 8B:
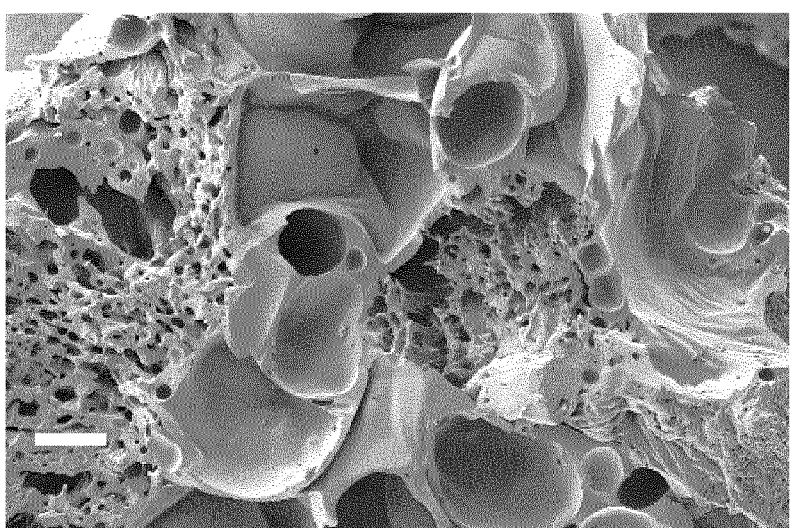
Figure 8C:
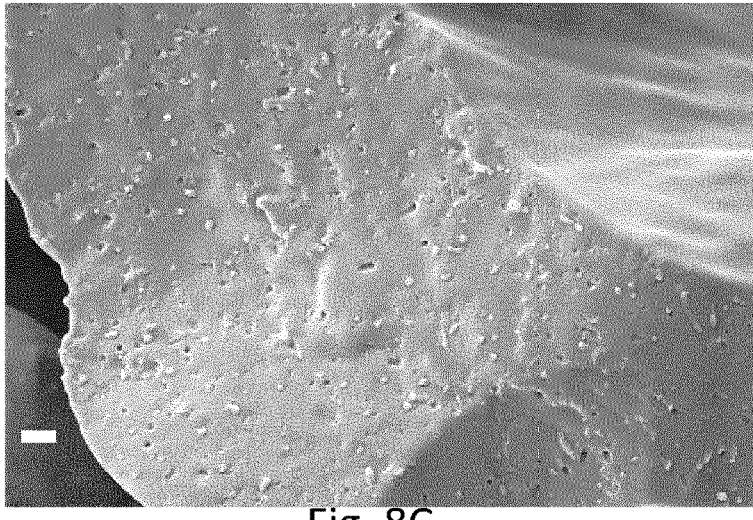

FIG. 8 A-C show scanning electron micrographs of cross sections of dried pellets. The dried pellets comprise an additive and microorganisms, *B. breve*.

FIG. 9 A-C show scanning electron micrographs of cross sections of milled pellets. The dried particles comprise an additive and microorganisms, *B. breve*.

EXAMPLE 1 MANUFACTURING OF DRIED PARTICLES COMPRISING *LACTOBACILLUS RHAMNOSUS* AND OTHER REPRESENTATIVE SPECIES

Figure 1:
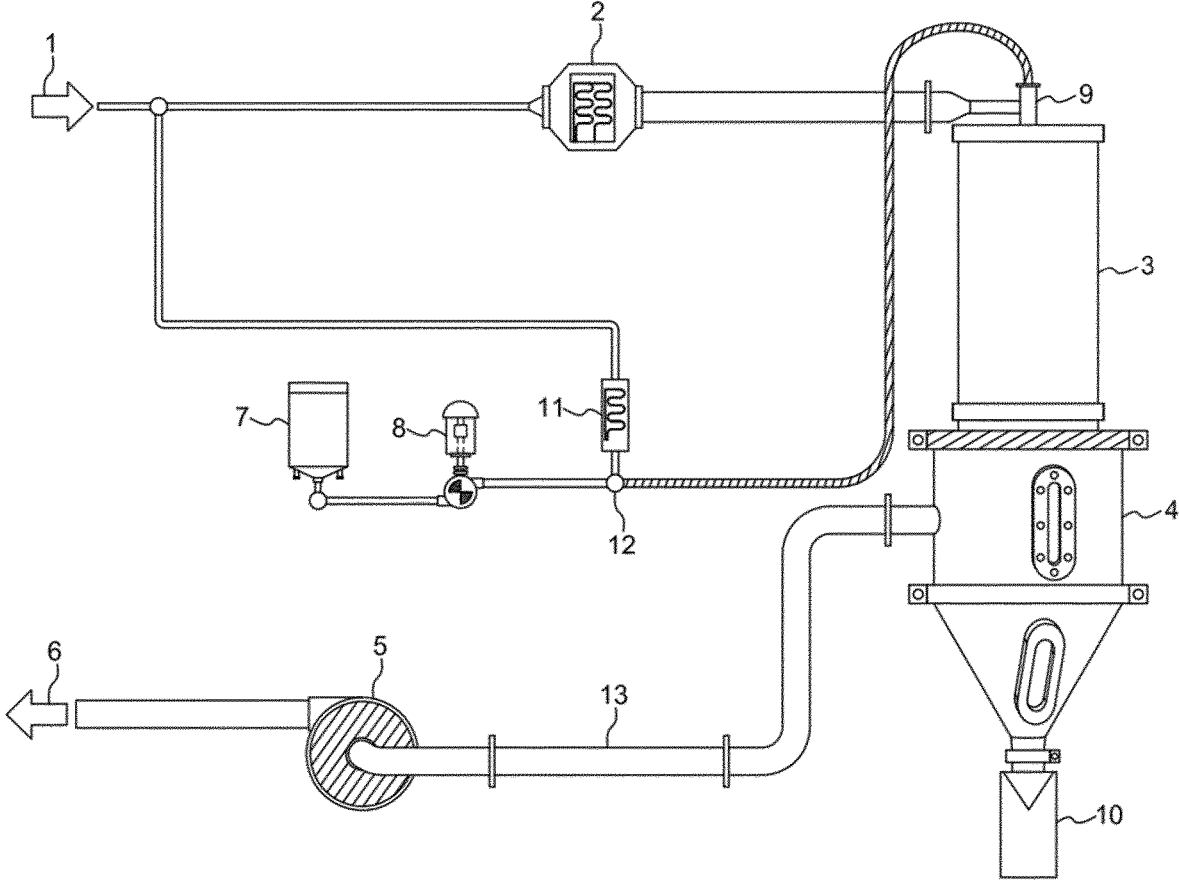
FIG. 1 shows a schematic illustration of an electrostatic spray dryer.

An electrostatic spray drier was used for manufacturing of dried particles comprising microorganisms. FIG. 1 shows a schematic illustration of the electrostatic spray dryer, where the main gas flow (1) was supplied by a N$_2$ battery. The electrostatic spray dryer was configured such that the main gas flow passed a heater (2) before it entered the top of the electrostatic spray dryer. The main gas flow entered the spray drying chamber (3) at an angle of approximately 30°. The main gas flow exited the spray dryer through two filters (4), which filtered the particles from the gas, before passing the ventilator (5) and was thereafter led to the exhaust (6).

The feedstock was pumped from the feed container (7) through a peristaltic Watson Marlow pump (8) to a two-fluid nozzle (9) at the top of the electrostatic spray dryer.

The atomized feedstock was dried co-current in the chamber (3) and was collected as dry powder in a glass container (10) at the end of the drying chamber.

The atomization was performed with pressurized N$_2$, which entered from the main gas flow (1), passed through a heater (11) and entered the two-fluid nozzle (9) at a controlled atomization pressure. A voltage generator (12) controlled the Pulse Width Modulation (PWM), and it was in electric contact with the two-fluid nozzle such that an electric charge could be applied to the suspension.

The spray dryer comprised an oxygen level sensor (13), and was configured to shut down if the oxygen level got too high.

To obtain the suspension, *Lactobacillus rhamnosus* (LGG®) was grown in a fermenter (Infors, Switzerland) using MRS (Oxoid) and concentrated using cross flow filtration (Repligen, The Netherlands). The total solid content of the suspension was 33.51%.

Electrostatic spray drying was performed at continuous stirring of the suspension, with a main air flow of 25 m³/h N$_2$. The supply gas pressure and temperature of N$_2$ was 80 bar(g) and 20.8° C. respectively. The inlet temperature (T$_{in}$) was kept at 80° C. and the outlet temperature (T$_{out}$) was kept at 38.3° C.

Atomization of the suspension (feedstock) was performed with a two-fluid nozzle, where the atomization pressure (P$_{nozzle}$) was 1.0 bar(g) N$_2$ and the temperature was 50° C. The feed rate was kept at approximately 4.1 g/min.

The electrostatic charge was applied to the suspension, by the use of an electrode in contact with the suspension, located prior to the nozzle, by Pulse Width Modulation (PWM), wherein a 5 kV square pulse, with a pulse length of 1 s, was provided every third second, with a baseline of 1 kV. The oxygen level in the drying chamber was kept at 0.5% O$_2$.

Figure 2:
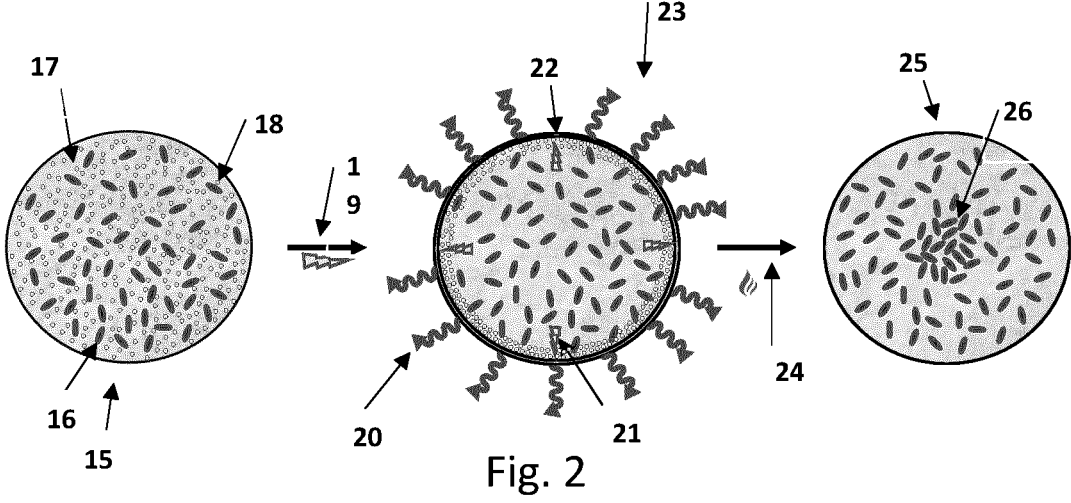
FIG. 2 shows a schematic illustration of the drying process in the electrostatic spray dryer

The electric charge, applied to the suspension by contacting the suspension with the electrode, enables partitioning of the components within the formed droplets, such as with respect to their polarity, as can be seen in FIG. 2. The droplets may thereby evaporate faster and/or have an improved encapsulation of the microorganism. Following atomization of the suspension droplets (15) were formed comprising bacterial cells (16), a drying protective matrix comprising a carrier material (17), and water (18). By application of the electrical charge (19) to the droplets, the polar ingredients migrated towards the surface of the electrically charged droplets (23). The surface of the droplets thereby comprised the major part of the electrical charge (21). This facilitated drying of the droplets as water, present at the surface of the droplets, could readily evaporate (20). The migration of water towards the surface of the droplets, resulted in a water layer (22) at the surface of the droplets. Following the formation of electrically charged droplets, comprising partitioned components, the evaporation rate was increased, compared to similar droplets without an electrical charge. The water thereby evaporated under the application of heat (24). Following drying of the solvent, dried particles (25) were formed that comprised a protective matrix, bacterial cells and a small amount of residual water. The bacterial cells were concentrated in the center of the dried particles. It could further be seen that the concentration of bacterial cells decreased towards the surface, i.e. the concentration of bacterial cells decreased radially, with the highest concentration in the center of the dried particles and no bacterial cells present at the surface of the dried particles.

Following drying, the dried particles were collected in a container at the outlet end of the drying chamber of the electrostatic spray dryer. As a control a sample of the suspension was pelletized by dripping into liquid nitrogen, collecting the pellets, freeze-drying these and milling the dry pellets into a powder.

Viability Analysis of Dried Particles

The viability of the microorganisms embedded within the manufactured dried particles, as described above, was analyzed using standard plate counting, and further compared to other methods for drying of microorganisms.

Figures 3A, 3B:
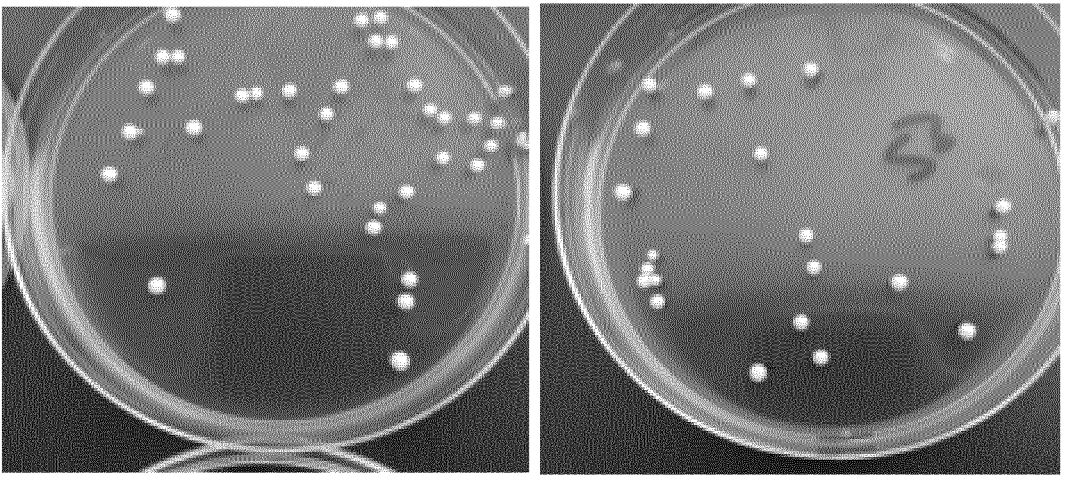
FIG. 3A-B show culture plate viability assays of dried particles comprising microorganisms.

Colonies formed from electrostatic spray dried particles and milled pellets material are shown in FIG. 3A-B respectively. The colonies formed from the milled LGG® pellets were significantly smaller compared to the electrostatic spray dried colonies.

Figure 4:
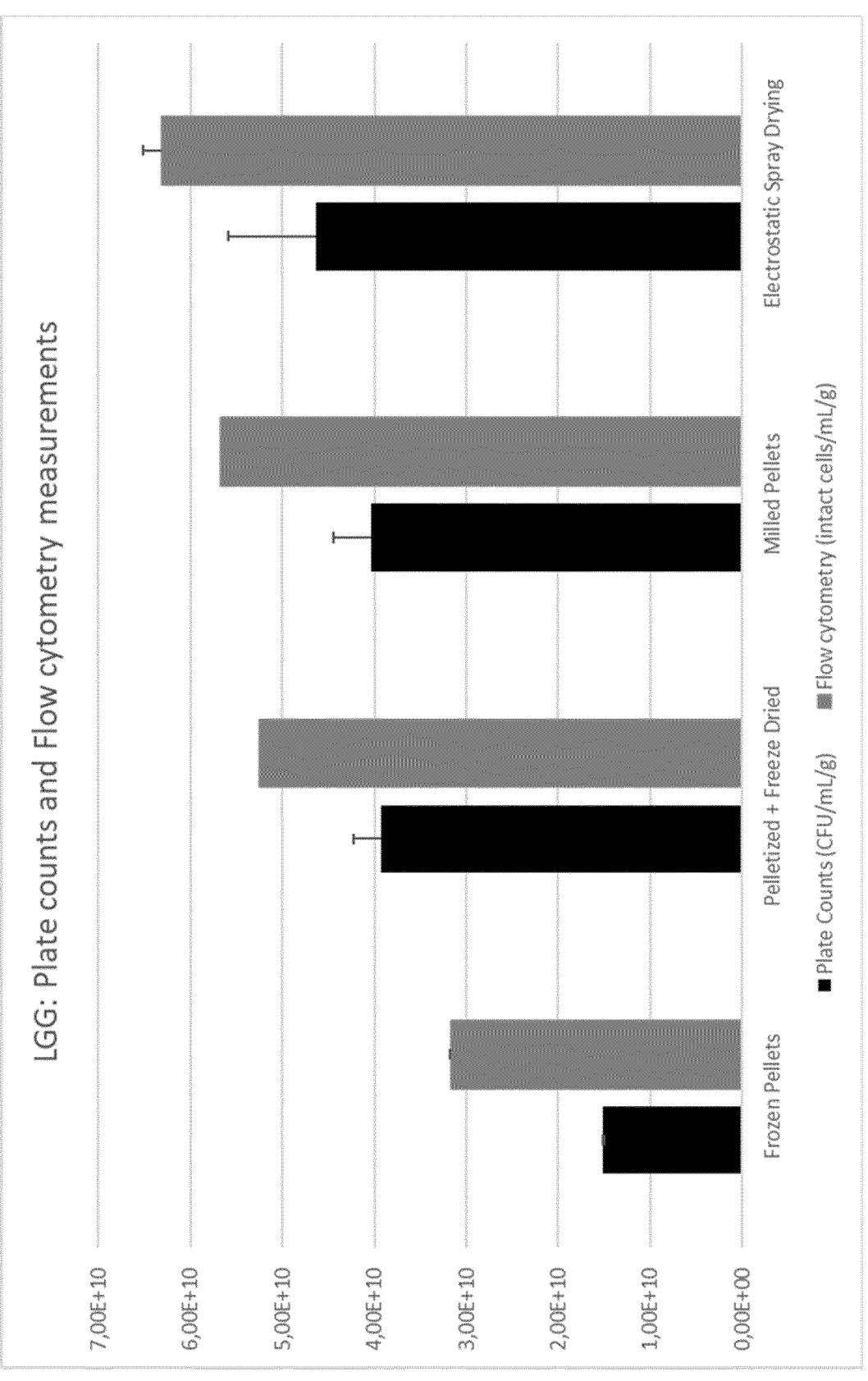
FIG. 4 shows viability data for dried particles produced by varying means of drying, and suspensions of *Lactobacillus rhamnosus* microorganisms.

The measured CFU/ml is shown in FIG. 4 (black bar) and is the mean CFU/ml of 3 samples for each process type. The CFU/ml was the highest for the electrostatic spray dried material, followed by the freeze dried pellets and the milled pellets.

Additionally, the MRS tubes where the serial dilutions were made in showed slower growth of LGG® for the milled product, compared to the electrostatic spray dried particles.

Flow Cytometry

Viability of the dried particles was measured using flow cytometry. The viability of the electrostatic dried material was compared to pelletized material, pelletized and freeze dried material, and milled material wherein the dried particles of each process had been formed from a similar suspension, comprising LGG®.

The flow cytometry results (FIG. 4, grey bars), was the average number of cells/ml, with the error bars showing the standard deviations. Each process was repeated three times.

The number of intact cells of the freeze dried LGG® pellets and the milled pellets were measured, and found to be in the same range, The highest number of intact cells/g was acquired by the electrostatic spray drying process.

SEM Micrographs

FIG. 5A-B show scanning electron micrographs of the electrostatic spray dried particles comprising LGG®. The particles thereby comprise an additive, such as a drying protectant, and microorganisms. FIG. 5A is a micrograph acquired at a magnification of 500× magnification (scale bar is 20 μm), while FIG. 5B is acquired at 2500× magnification (scale bar is 2 μm). The particles can be seen to have relatively spherical and smooth surfaces, and there were no microorganisms (bacteria) present on the surfaces of the particles.

To investigate the interior of the particles, electrostatically spray dried particles were split such that their cross sections were revealed and thereafter analyzed by SEM, FIG. 6A-B (scale bars are 2 μm). The bacteria can be seen to be fully embedded within the additive, and not present on the surface of the dried particle. Thereby, the bacterial cells were not exposed to the surroundings at the surface of the dried particles, but instead protected within the additive/drying protectant. Furthermore, the particle was compact, with a low volume fraction of internal voids. Thereby, the total volume of the microorganisms and the additive was similar to the volume of the entire dried particles, i.e. the volume fraction of the microorganisms and the additive (to the dried particle) was large.

It was also seen that there was a small layer of material on the surface of the particle, that was free of bacterial cells and the bacterial cells were therefore not exposed to the surroundings.

The fact that the bacterial cells were protected by a material layer, could result in a better stability of the electrostatic spray dried powder, compared to the other particles where some of the bacterial cells were exposed to the surroundings at the surface of the particles.

EXAMPLE 2 PELLETIZING, FREEZE DRYING, MILLING AND ELECTROSTATIC SPRAY DRYING OF B. BREVE

The primary objective of this test was to characterize and compare electrostatic spray dried B. breve with pelletized, freeze dried and milled B. breve. The difference in viability of the dried powder from each process was evaluated.

Materials and Method

Electrostatic Spray Drying

Electrostatic spray drying was carried out identical to Example 1.

To obtain the suspension, Bifidobacterium breve was grown in a fermenter (Infors, Switzerland) using MRS (Oxoid) and concentrated using cross flow filtration (Repligen, The Netherlands).

Cross Flow Filtration

The fermentate was pumped directly from the fermenter to the cross flow filtration unit. The retentate was pumped back to the fermenter while the permeate was collected. The process was allowed to continue until the desired concentration was achieved or until the retentate was too viscous for further pumping.

Following concentration, the concentrate was measured to have a total solid content of 8.50% (w/w) (Mettler Toledo: 105° C.—1 mg/50 s).

Additives, such as drying protectants, suitable for protecting microorganisms during cryogenic freezing were added to the suspension. These additives were added such that the ratio between the total solid content of the concentrate and total solid content of these additives were 1:4. The additive used was sucrose.

After the additives were added to the concentrate, total solids were measured again, but due to the large amounts of sugar added, it was decided to perform the total solids measurement at 60° C. instead of 105° C., in order not to burn the sugars and thereby getting a false result.

Total solid content of the suspension was measured to be 26.09% (w/w) (Mettler Toledo: 60° C.—1 mg/140 s).

Pelletizing and Freeze Drying

A concentrated B. breve fermentate comprising drying protectant (sucrose) was pelletized and subsequently freeze dried.

Pelletizing was performed without atomization gas and the feed rate was controlled by the Watson Marlow pump, set to approximately 13.86 ml/min.

The pelletized material was collected by a 50 μm sieve from Retsch and thereafter the collected pelletized material was transferred to a plastic container and kept cold on dry ice until it was transferred to an anaerobic glovebox.

For freeze drying, the pelletized material was evenly distributed to a metal freeze drying trays, and freeze dried (Martin Christ Gefriertrocknungsanlagen GmbH) for 46 hours and 10 minutes. The freeze dried material was loaded to a small aluminum bag, which subsequently was welded.

The Freeze Dried Pellets:

Water activity $(a_w)$=0.152 at 21.44° C.

Residual moisture=0.44% (Mettler Toledo: 60° C.—1 mg/140 s)

It was not possible to measure particle size distribution on the freeze dried pellets, because they were too big.

Milling of Freeze Dried Pellets:

The milling was performed manually in a mortar for approximately 5 minutes.

Properties of the Milled Pellets:

Water activity $(a_w)$=0.142 at 21.53° C.

Residual moisture=0.84% (Mettler Toledo: 60° C.—1 mg/140 s)

Mean particle size distribution $(d_{50})$=150 μm Span=5.174

Electrostatic Spray Drying

Electrostatic spray drying was performed at continuous stirring of the suspension, comprising B. breve and drying protectant, with a main air flow of 25 m³/h N₂. The supply gas pressure and temperature of N₂ was 80 bar(g) and 21.5° C. respectively. The inlet temperature $(T_{in})$ was kept at 80° C. and the outlet temperature $(T_{out})$ was kept at 36° C.

Atomization of the suspension (feedstock) was performed with a two-fluid nozzle, where the atomization pressure $(P_{nozzle})$ was 1.0 bar(g) N₂ and the temperature was 50° C.

The feed rate was kept at approximately 4.1 g/min. The drying chamber had a vacuum pressure of 0.3 kPa. The dried particles were collected at the outlet end of the drying chamber, and analyzed. As mentioned above, the total solid content of the *B. breve* concentrate comprising drying protectant, i.e. the suspension before drying, was 26.09%.

Results

Most Probable Number (MPN):

Growth was measured on the fermentate, concentrate, concentrate+drying protectant, frozen pellets, freeze dried pellets, milled pellets and electrostatic spray dried material.

The cell count pr. ml or cell count pr. gram of all the samples was an average of six analytical results.

| Process step | MPN pr. mL or pr. g | Log₁₀ MPN | 95% confidence limits Lower | Upper |
|---|---|---|---|---|
| FM | 3.9E+10 | 10.6 | 1.4E+10 | 1.1E+11 |
| Concentrate | 2.2E+11 | 11.4 | 9.1E+10 | 5.6E+11 |
| Concentrate and drying protectant | 2.2E+11 | 11.4 | 9.1E+10 | 5.6E+11 |
| Frozen pellets | 7.8E+10 | 10.9 | 2.6E+10 | 2.3E+11 |
| Freeze dried pellets | 2.9E+10 | 10.5 | 1.1E+10 | 7.9E+10 |
| Milled pellets | 4.0E+10 | 10.6 | 1.8E+10 | 9.0E+10 |
| Electrostatic spray dried | 5.8E+11 | 11.8 | 1.9E+11 | 1.8E+12 |

High MPN numbers were seen in all samples and all steps of the process. It was seen from the above table that MPN decreased during pelletizing. Electrostatic spray drying, on the other hand, resulted in high MPN, about an order of magnitude higher than the pelletized materials.

It was also seen that the MPN decreased during the freeze drying step and it was the milled pellets that had the highest MPN of the freeze dried samples.

Flow Cytometry

Flow cytometry was measured on the pre-fermentate, the frozen pellets, the freeze dried pellets, the milled pellets, and the electrostatic spray dried material.

| Sample | Damaged | Intermediate cells/ml or cells/g | Intact | Total | Intact % |
|---|---|---|---|---|---|
| Pre-fermentate (PFM) | $3.57 \cdot 10^7$ | $1.71 \cdot 10^8$ | $3.16 \cdot 10^8$ | $5.23 \cdot 10^8$ | 60.4 |
| Pellets (frozen) | $1.52 \cdot 10^{10}$ | $4.99 \cdot 10^9$ | $2.24 \cdot 10^9$ | $2.25 \cdot 10^{10}$ | 10.0 |
| Freeze dried pellets | $9.16 \cdot 10^9$ | $3.26 \cdot 10^{10}$ | $7.98 \cdot 10^{10}$ | $1.22 \cdot 10^{11}$ | 65.6 |
| Milled pellets | $1.11 \cdot 10^{10}$ | $3.44 \cdot 10^{10}$ | $7.40 \cdot 10^{10}$ | $1.20 \cdot 10^{11}$ | 61.6 |
| Electrostatic spray dried | $6.78 \cdot 10^9$ | $2.07 \cdot 10^{10}$ | $1.03 \cdot 10^{11}$ | $1.30 \cdot 10^{11}$ | 79.3 |

As it was seen from the flow cytometry results, there was a high number of total cells in all the analyzed samples.

It can be seen from the above table that the number of total cells/g in the dried powders were comparable. It was seen that there was a slight decrease in intact cells/g when the freeze dried pellets were milled. This was also seen in the CFU analysis.

It can also be seen that the intact cells/g was higher for the electrostatic spray dried powder compared to the freeze dried powders (freeze dried pellets and milled pellets).

From the viability analysis it can be seen that the MPN and flow cytometry results were very well correlated with each other and the CFU results were approximately 1 log lower when comparing MPN to flow cytometry.

SEM Micrographs

From all the powder samples produced, SEM pictures were produced.

Figure 7A:
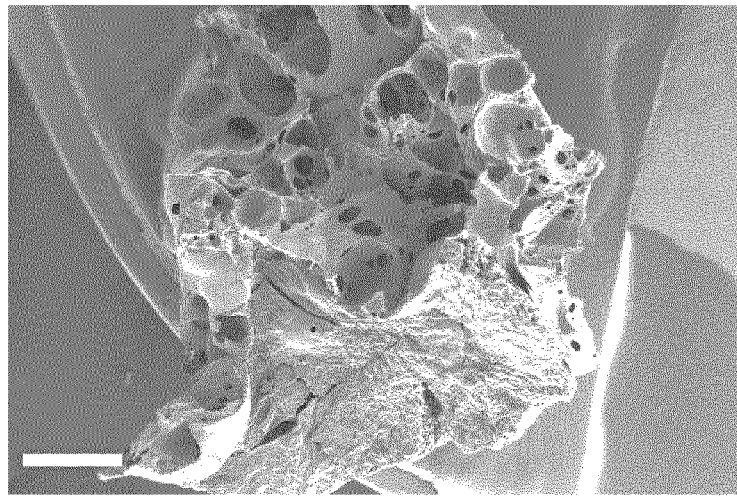
Figure 7B:
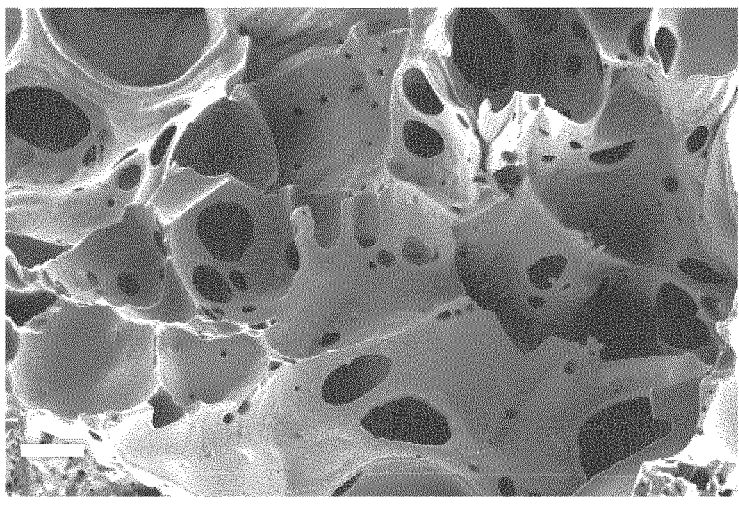
Figure 7C:
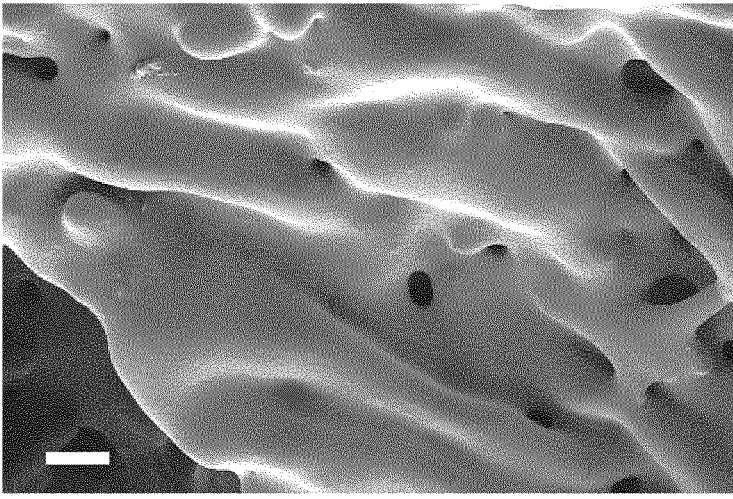

SEM pictures were taken of the surface of the particles, but the particles were also cut in half and SEM pictures of inside of the pellets were taken. FIG. 7A-C show intact pellets at a magnification of 16× (scale bar 1 mm), 50× (scale bar 200 μm) and 500× (scale bar 20 μm) respectively.

The pellet surfaces differ between different pellets, wherein the number of cavities and the smoothness of the surface vary significantly. Broken off areas, typically sharp edges of the pellets, were abundant. Bacteria can be seen both inside and on the surface of the pellets.

The micrographs of cut pellets (FIG. 8A-C) acquired at a magnification of 17× (scale bar 1 mm), 50× (scale bar 200 μm) and 2500× (scale bar 2 μm) reveal a large variation between areas within the pellets, mainly in terms of their densities. Some areas can be seen to comprise large cavities while other denser areas only comprise small channels.

Figure 9A:
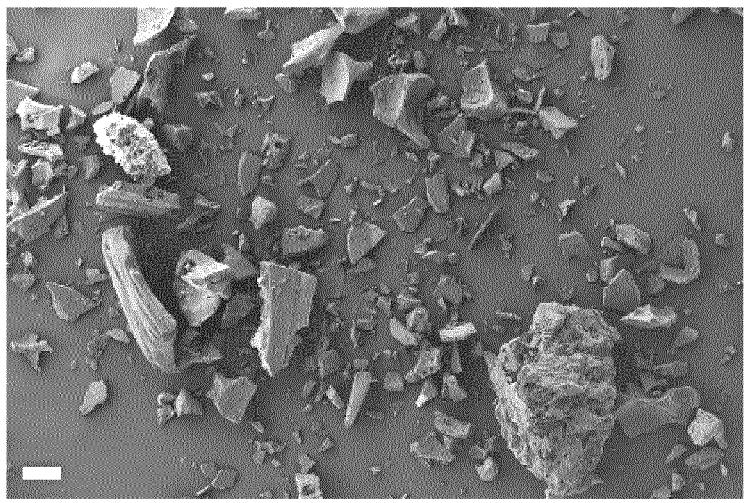
Figure 9B:
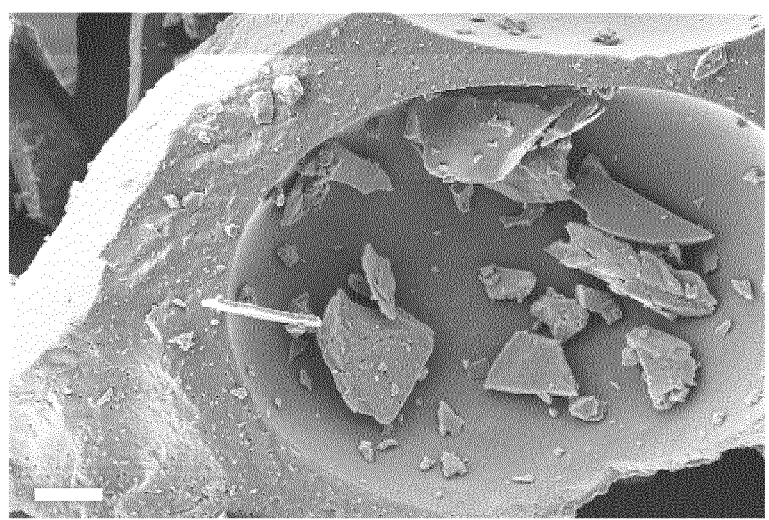
Figure 9C:
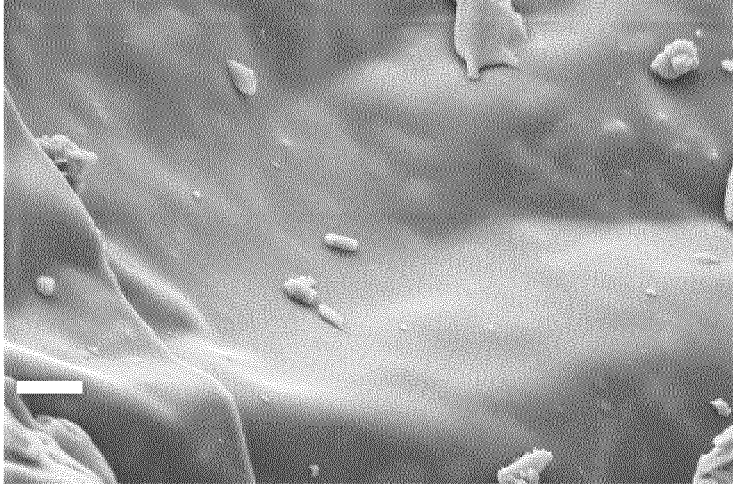

Milled pellets, FIG. 9A-C, acquired at a magnification of 50× (scale bar 100 μm), 1000× (scale bar 10 μm) and 5000× (scale bar 2 μm) respectively, can be seen to have a varied morphology with flat surfaces and sharp edges. The milled pellets can also be seen to have a big difference in particle size, which was also apparent from the mean particle size distribution analysis.

The SEM micrographs reveal that bacterial cells were present on all surfaces of the milled pellets, meaning that there was a higher number of bacteria cells that were exposed to the surroundings compared to the un-milled pellets, which could result in a decreased stability of the milled pellets.

EXAMPLE 3 PELLETIZING, FREEZE DRYING, MILLING AND ELECTROSTATIC SPRAY DRYING OF *F. PRAUSNITZII*

The main objective of the performed tests was to characterize and compare the viability of electrostatic spray dried *F. prausnitzii* with the powder obtained from freeze dried pellets and milled freeze dried pellets.

Materials and Methods

Cross Flow Filtration

The fermentate was pumped directly from the fermenter to the cross flow filtration unit.

The retentate was pumped back to the fermenter while the permeate was collected.

This process was allowed to continue until the desired concentration was achieved or until the retentate was too viscous for further pumping.

Pelletizing and Freeze Drying

The liquid feed was pumped from a feed container through a Watson Maslow peristaltic pump to a nozzle. The liquid material was dripping from the nozzle into liquid nitrogen (LN₂) placed under the nozzle. The container for LN₂ was used to add extra LN₂ to the frozen product container during the experiment. The pelletized material was thereafter filtered through a 50 μm Retsch filter, where the frozen pellets were collected.

For freeze-drying, pelletized material was separated from the LN₂ by the filter, the pellets were thereafter loaded onto freeze drying trays or glass petri dishes and subsequently freeze dried.

Electrostatic Spray Drying

Electrostatic spray drying was carried out identical to Example 1.

Experimental Work

A culture of *F. prausnitzii* was grown in a fermenter (Infors) using media as described in Duncan et al., Growth requirements and fermentation products of *Fusobacterium prausnitzii*, and a proposal to reclassify it as *Faecalibacterium prausnitzii* gen. nov., comb. nov. Int. J. Syst. Evol. Microbiol. 52, 2141-2146 (2002).

The fermentate was concentrated by Cross flow filtration (CFF), initiated at pH=5.54 and was performed with a fermentate temperature of 37° C.

Cross flow filtration was slowly started with a feed flow of 180 ml/min. and within approximately 7 minutes the feed rate was gradually increased to 1000 ml/min.

At a feed flow of 1000 ml/min., inlet pressure ($P_{in}$) was 0.37 bar(g), TMP was 0.21 bar(g) and permeate flow ($Q_{permeate}$) was 120 ml/min. and the shear rate was 1450 $s^{-1}$.

After approximately 9 minutes the back pressure valve was activated with a TMP setpoint of 0.50 bar(g).

Corresponding $P_{in}$ was 0.60 bar(g), $Q_{permeate}$=125 ml/min. and shear rate=1080 $s^{-1}$.

After additional 13 minutes the TMP setpoint was changed to 0.60 bar(g).

Corresponding $P_{in}$ was 0.75 bar(g), $Q_{permeate}$ was 126 ml/min and the shear rate was 1080 $s^{-1}$.

In the end of the concentration process, foam was seen in the fermenter, which was due to the high feed rate used.

Approximately 1 hours and 30 minutes after the start, $P_{inlet}$ had increased to 0.85 bar(g) and a concentration factor of at least 30× was reached.

Following concentration, the concentrate was measured to have a total solid content of 12.55% (Mettler Toledo: 105° C.—1 mg/50 s)

Additives, such as drying protectants, suitable for protecting microorganisms during cryogenic freezing were added to the suspension. These additives (sucrose in the present case) were added such that the ratio between the total solid content of the concentrate and total solid content of these additives were 1:4.

TS of concentrate with drying protectant=31.83% (Mettler Toledo: 60° C.—1 mg/140 s)

Pelletizing and Freeze Drying

A concentrated *F. prausnitzii* fermentate comprising drying protectant was pelletized and freeze dried. Pelletizing was performed without atomization gas and the feed rate was controlled by the Watson Marlow pump, which was set to 2 RPM, which corresponds to approximately 13.86 ml/min. The pelletizing process took 16 minutes. The pelletized material was collected by a 50 μm sieve from Retsch.

During the pelletizing process, it was seen that the frozen pellet size was very un-uniform, and the size was varying very much. There were seen some very big pellets and there were also some small pellets.

The collected pelletized material was transferred to a plastic container and kept cold on dry ice until it was transferred to the anaerobic glovebox and thereafter loaded to a freeze drier (Martin Christ).

After 46 hours and 10 minutes the freeze drying was ended, and the freeze dried material was removed from the freeze drying tray.

The freeze dried material was loaded to a small aluminum bag, which subsequently was welded.

Properties of the Freeze Dried Pellets:

Water activity ($a_w$) was measured at room temperature.

Water activity ($a_w$)=0.078

Residual moisture=0.41% (Mettler Toledo: 60° C.—1 mg/140 s)

It was not possible to measure particle size distribution on the freeze dried pellets, because they were too big.

Milling of Freeze Dried Pellets:

The milling was performed manually in a mortar for approximately 5 minutes.

Properties of the Milled Pellets:

Water activity ($a_w$)=0.074

Residual moisture=0.94% (Mettler Toledo: 60° C.—1 mg/140 s)

Mean particle size distribution ($d_{50}$)=833 μm

Span=2.547

It was seen from the particle size distribution that the mean particle size of the milled pellets was much larger compared to the freeze dried mean particle size, but the span was in the same range.

Electrostatic Spray Drying

During electrostatic spray drying the feed was kept under steering. *F. prausnitzii* concentrate comprising drying protectant was electrostatic spray dried.

Electrostatic spray drying was performed with a main air flow of 25 $m^3$/h $N_2$. The supply gas pressure and temperature of $N_2$ was respectfully 80 bar(g) and 21.5° C. The inlet temperature ($T_{in}$) was 80° C. and the outlet temperature ($T_{out}$) was 36° C.

Atomization of the feed was performed with a two-fluid nozzle, where the atomization pressure ($P_{nozzle}$) was 1.0 bar(g) $N_2$ and the temperature was 50° C.

The feed rate was controlled by a peristaltic pump with and RPM of, which corresponds to approximately 4.8 g/min.

The electrostatic charge was applied to the suspension, by the use of an electrode in contact with the suspension, located prior to the nozzle. Pulse Width Modulation (PWM) was used, wherein a 5 kV square pulse, with a pulse length of 1 s, was provided every third second, with a baseline of 1 kV.

During the entire test the oxygen level in the chamber was 0.5% oxygen. The drying chamber had a vacuum pressure of 0.3 kPa. After the test was ended, dried particles were collected at the outlet end of the drying chamber and analyzed. As mentioned above, the total solid content of the *F. prausnitzii* concentrate with drying protectant, i.e. the suspension before drying, was 31.83%.

Properties of the Electrostatic Spray Dried Product:

Water activity ($a_w$)=0.245 at 21.78° C.

Residual moisture=3.67% (Mettler Toledo: 60° C.—1 mg/140 s)

Mean particle size distribution ($d_{50}$)=28.0 μm

Span=2.461

Results

Particle Analytics

For all the produced samples, residual moisture ($R_M$ %), water activity ($a_w$), particle size distribution ($d_{50}$ and span) were measured.

Viability was also measured for all produced samples.

Viability was measured by CFU (Colony Forming Units), MPN (Most Probable Number) and flow cytometry.

| Sample | $a_w$ | $R_M$ % | $d_{50}$ | Span |
|---|---|---|---|---|
| Freeze-dried pellets | 0.078 | 0.40 | — | — |
| Milled pellets | 0.074 | 0.94 | 833 μm | 2.547 |
| Electrostatic spray dried | 0.245 | 3.67 | 28 μm | 2.461 |

It was seen from the analytical results in the table above, that the water activity was higher for the electrostatic spray dried powder than for the pellets and milled pellets. Mean particle size distribution was large for the milled pellets.

From the Malvern data measurements it was seen that the mean particle size distribution of the milled pellets was higher than the mean particle size distribution of the electrostatic spray dried powder and the span of the powders were in the same range.

Most Probable Number (MPN):

Growth was measured on the fermentate, concentrate, concentrate+drying protectant, pelletized material and electrostatic spray dried material.

The cell count pr. ml or cell count pr. gram of all the samples was an average of six analytical results.

| | MPN | Log₁₀ | 95% confidence limits | |
|---|---|---|---|---|
| Process step | pr. mL or pr. g | MPN | Lower | Upper |
| Fermentate | $2.9 * 10^9$ | 9.5 | $1.1 * 10^9$ | $7.9 * 10^9$ |
| Concentrate | $1.2 * 10^{11}$ | 11.0 | $4.2 * 10^{10}$ | $3.3 * 10^{11}$ |
| Concentrate and drying protectant | $1.3 * 10^9$ | 9.1 | $5.2 * 10^8$ | $3.3 * 10^9$ |
| Frozen pellets | $1.7 * 10^8$ | 8.2 | $6.6 * 10^7$ | $4.6 * 10^8$ |
| Freeze dried pellets | $3.7 * 10^8$ | 8.6 | $1.5 * 10^8$ | $1.1 * 10^9$ |
| Milled pellets | $5.3 * 10^7$ | 7.7 | $2.0 * 10^7$ | $1.7 * 10^8$ |
| Electrostatic spray dried | $2.2 * 10^8$ | 8.3 | $8.9 * 10^7$ | $5.4 * 10^8$ |

From the MPN results it could be seen that the viability decreased 87% during pelletizing. It could also be seen that the freeze dried pellets and the electrostatic spray dried powder was in the same range, with the freeze dried pellets slightly higher. From the MPN results it was seen that the viability decreased 69% during the milling step.

Colony Forming Units (CFU)

For all CFU measured samples, no forging colonies was observed, strongly indicating that no contaminations were in the analyzed samples. In the table below the analytical results can be seen.

| Process step | CFU count (cells/mL) | Log |
|---|---|---|
| FM | $3.07 \cdot 10^8$ | 8.5 |
| Concentrate | $1.02 \cdot 10^9$ | 9.0 |
| Concentrate + drying protectant | $4.97 \cdot 10^7$ | 7.7 |
| Pellets (frozen) | $8.27 \cdot 10^6$ | 6.9 |
| Freeze dried pellets | $1.86 \cdot 10^6$ | 6.3 |
| Milled freeze dried pellets | $6.90 \cdot 10^5$ | 5.8 |
| Electrostatic spray drying | $1.77 \cdot 10^6$ | 6.2 |

As it was seen from the CFU results, CFU/mL decreased 83% during pelletizing. It was also seen that the CFU/mL was in the same range for freeze dried pellets and electrostatic spray dried powder. During milling of the pellets there was a 63% decrease in CFU/mL, which also correlates with the results seen from the MPN analysis.

Flow Cytometry

Flow cytometry was measured on the fermentate, pelletized material and electrostatic spray dried material.

| | Damaged | Intermediate | Intact | Total | Intact |
|---|---|---|---|---|---|
| Sample | | cells/ml or cells/g | | | % |
| Fermentate (PFM) | $1.46 \cdot 10^8$ | $1.63 \cdot 10^8$ | $1.50 \cdot 10^9$ | $1.81 \cdot 10^9$ | 82.9 |
| Pellets (frozen) | $2.84 \cdot 10^{10}$ | $5.58 \cdot 10^9$ | $7.48 \cdot 10^8$ | $3.47 \cdot 10^{10}$ | 2.2 |

-continued

| | Damaged | Intermediate | Intact | Total | Intact |
|---|---|---|---|---|---|
| Sample | | cells/ml or cells/g | | | % |
| Freeze dried pellets | $8.05 \cdot 10^{10}$ | $9.00 \cdot 10^8$ | $4.00 \cdot 10^8$ | $8.18 \cdot 10^{10}$ | 0.49 |
| Milled pellets | $9.12 \cdot 10^{10}$ | $8.16 \cdot 10^8$ | $2.04 \cdot 10^8$ | $9.22 \cdot 10^{10}$ | 0.21 |
| Electrostatic spray dried | $7.12 \cdot 10^{10}$ | $7.65 \cdot 10^8$ | $4.93 \cdot 10^8$ | $7.25 \cdot 10^{10}$ | 0.68 |

As it was seen from the flow cytometry results in the table above, there was a high number of total *F. prausnitzii* cells in all the analyzed samples.

It was seen from the above table that the number of total cells/g in the electrostatic spray dried powder was slightly lower than that of the milled powder and the freeze dried pellets.

The electrostatic spray dried powder had the highest number of intact cells/g, and also the highest intact percentage, which was correlated to the number of total cells/g in the individual sample. It was seen that the viability decreased 49% when the freeze dried pellets were milled. This was in correlation with what was also observed in the MPN and CFU analysis.

EXAMPLE 4 PELLETIZING, FREEZE DRYING, MILLING AND ELECTROSTATIC SPRAY DRYING OF *B. THETAIOTAOMICRON*

The primary objective of this test was to characterize and compare electrostatic spray dried *Bacteroides thetaiotaomicron* with pelletized, freeze dried and milled *B. thetaiotaomicron*. The characterization of the products included measurements of the respective viabilities of the dried powder from each process.

Materials and Methods

Cross flow filtration was carried out identical to Example 3. Two separate fermenters were used. Pelletizing and Freeze Drying were carried out identical to Example 3. Electrostatic spray drying was carried out identical to Example 1.

Experimental Work

A culture of *B. thetaiotaomicron* was grown in a fermenter (Infors) using media as described in Taketani et al., A Phase-Variable Surface Layer from the Gut Symbiont *Bacteroides thetaiotaomicron*, mBio. 2015 September-October; 6(5): e01339-15. The fermentate was concentrated by Cross Flow Filtration in Fermenter A or Fermenter B as described below.

Fermenter A

Cross flow filtration was initiated at pH=5.20 and was performed with a fermentate temperature of 37° C. Total solids of the fermentate before concentration were 5.82% (Mettler Toledo: 105° C.—1 mg/50 s).

Cross flow filtration was slowly started with a feed flow of 280 ml/min. and within approximately 4 minutes the feed rate was gradually increased to 1680 ml/min. At a feed flow of 1680 ml/min., inlet pressure ($P_{in}$) was 0.07 bar(g), TMP was 0.11 bar (g) and permeate flow ($Q_{permeate}$) was 152 ml/min. and the shear rate was 2500 s$^{-1}$. After 13 minutes the back pressure valve was activated with a TMP setpoint of 0.30 bar (g). Corresponding $P_{in}$ was 0.24 bar (g), $Q_{permeate}$=200 ml/min. and shear rate=2475 s$^{-1}$. The concentration was stopped after approximately 1 hours and 37 minutes.

Fermenter B

Cross flow filtration (CFF) was initiated at pH=5.12 and was performed with a fermentate temperature of 37° C. Total solids of the fermentate before concentration were 5.82% (Mettler Toledo: 105° C.—1 mg/50 s).

Cross flow filtration was slowly started with a feed flow of 280 ml/min. and within approximately 4 minutes the feed rate was gradually increased to 1680 ml/min. At a feed flow of 1680 ml/min., inlet pressure ($P_{in}$) was 0.06 bar(g), TMP was 0.17 bar (g) and permeate flow ($Q_{permeate}$) was 190 ml/min. and the shear rate was 2450 $s^{-1}$. After 12 minutes the back pressure valve was activated with a TMP setpoint of 0.30 bar (g).

Corresponding $P_{in}$ was 0.27 bar (g), $Q_{permeate}$=195 ml/min. and shear rate=2446 $s^{-1}$.

The concentration was finished after approximately 1 hours and 11 minutes.

The collected concentrate from fermenter A and fermenter B was mixed, in total a concentration factor of 25.4 was reached. Total solids (TS) of concentrate=11.72% (Mettler Toledo: 105° C.—1 mg/50 s)

Additives, drying protectants, suitable for protecting microorganisms during cryogenic freezing were added to the suspension. These additives (sucrose in the present case) were added such that the ratio between the total solid content of the concentrate and total solid content of these additives were 1:4. TS of concentrate with drying protectant was 31.09% (Mettler Toledo: 60° C.—1 mg/140 s).

Pelletizing and Freeze Drying

A concentrated *B. thetaiotaomicron* fermentate comprising drying protectants was pelletized and freeze dried. Pelletizing was performed without atomization gas and the feed rate was controlled by the Watson Marlow pump, which was set to 2 RPM, which corresponds to approximately 13.86 ml/min. The pelletized material was collected by a 50 µm sieve from Retsch.

The collected pelletized material was transferred to an aluminum bag and kept cold on dry ice until it was transferred to the anaerobic glovebox and thereafter loaded to a freeze drier (Martin Christ).

After 46 hours and 10 minutes the freeze drying was ended, and the freeze dried material was removed from the freeze drying tray. The freeze dried material was loaded to a small aluminum bag, which subsequently was sealed by welding.

Properties of the Freeze Dried Pellets:

Water activity ($a_w$)=0.131 at 23.00° C.

Residual moisture=0.21% (Mettler Toledo: 60° C.—1 mg/140 s)

It was not possible to measure particle size distribution on the freeze dried pellets, because they were too big.

Milling of Freeze Dried Pellets:

The milling was performed manually in a mortar for approximately 5 minutes.

Properties of the Milled Pellets:

Water activity ($a_w$)=0.216 at 22.0° C.

Residual moisture=1.18% (Mettler Toledo: 60° C.—1 mg/140 s)

Mean particle size distribution ($d_{50}$)=195 µm

Span=3.880

As was seen from the obtained water activity, $a_w$ increased considerably during milling of the pellets.

Electrostatic Spray Drying

During electrostatic spray drying the feed was kept under steering.

*B. thetaiotaomicron* concentrate with drying protectant was electrostatic spray dried.

Electrostatic spray drying was performed with a main air flow of 25 $m^3$/h $N_2$. The inlet temperature ($T_{in}$) was 80° C. and the outlet temperature ($T_{out}$) was in the range of 37.0° C. to 38.5° C. Atomization of the feed was performed with a two-fluid nozzle, where the atomization pressure ($P_{nozzle}$) was 2.0 bar(g) $N_2$ and the atomization temperature was 50° C. The feed rate was controlled by a peristaltic pump with RPM in the range of 6 to 8, which corresponds to approximately 3.5 g/min to 5.5 g/min.

A two-fluid nozzle was used. The electrostatic charge was applied to the suspension, by the use of an electrode in contact with the suspension, located inside the nozzle prior to the nozzle tip where the liquid suspension is atomized into droplets. Pulse Width Modulation (PWM) was used, wherein a 5 kV square pulse, with a pulse length of 1 s, was provided every third second, with a baseline of 1 kV.

During the entire test the oxygen level in the chamber was 0.5% oxygen. The chamber had a vacuum pressure of 0.31 kPa. After the test was ended, dried particles were collected at the outlet end of the drying chamber and analyzed.

Properties of the Electrostatic Spray Dried Product:

Water activity ($a_w$)=0.140

Residual moisture=1.85% (Mettler Toledo: 60° C.—1 mg/140 s)

Mean particle size distribution ($d_{50}$)=8.61 µm

Span=5.219

Results

Particle Analytics

For all the produced samples, residual moisture ($R_M$ %), water activity ($a_w$), particle size distribution ($d_{50}$ and span) were measured. In addition, viability was measured for all produced samples by MPN (Most Probable Number) and flow cytometry.

| Sample | $a_w$ | $R_M$ % | $d_{50}$ | Span |
|---|---|---|---|---|
| Pellets | 0.131 | 0.21 | — | — |
| Milled pellets | 0.216 | 1.18 | 195 µm | 3.880 |
| Electrostatic spray dried | 0.140 | 1.85 | 8.61 µm | 5.219 |

The table above shows that the measured water activity was much higher for the milled pellets than for the other samples. Milling increased the water activity considerably. It was not possible to measure the mean particle size of the freeze dried pellets, because the pellets were too large for the Malvern Mastersizer 3000 analytical equipment.

Most Probable Number (MPN):

Growth was measured on the fermentate, concentrate, concentrate+drying protectant, pelletized material, freeze dried pellets, milled pellets, and electrostatic spray dried material.

The cell count pr. ml or cell count pr. gram of all the samples was an average of six analytical results.

| Process step | MPN [pr. mL or pr. g] | $Log_{10}$ MPN | Standard deviation |
|---|---|---|---|
| Fermenter A | 2.8E+09 | 9.4 | 1.0E+08 |
| Fermenter B | 1.5E+09 | 9.2 | 2.0E+09 |
| Concentrate | 5.0E+10 | 10.7 | 4.0E+10 |
| Conc. + drying protectant | 1.3E+10 | 10.1 | 1.3E+10 |
| Frozen pellets | 5.5E+06 | 6.7 | 6.4E+06 |
| Freeze dried pellets | 1.2E+06 | 6.1 | 1.5E+06 |
| Milled pellets | 4.8E+04 | 4.7 | 4.2E+03 |
| Electrostatic spray dried | 4.7E+07 | 7.7 | 3.1E+04 |

From the performed MPN tests it could be seen that the viability of *B. thetaiotaomicron* decreased during the freezing step; the viability was decreased by 3.4 log during pelletizing. In addition, during the freeze drying step, the viability of the pellets was reduced 0.6 log. It was also seen that the viability of the freeze dried pellets was decreased by 1.4 log during the milling of the pellets.

From the MPN results it was seen that the electrostatic spray dried powder had the highest viability, followed by the freeze dried pellets. The electrostatic spray dried powder had a viability that was 1.6 log higher compared to the viability of the freeze dried pellets and 3.0 log higher compared to the milled pellets.

Flow Cytometry

Flow cytometry was measured on the fermentate, concentrate, pelletized material, freeze dried pellets, milled pellets and electrostatic spray dried material.

Experimental Work

A culture of *E. hallii* was grown in a fermenter (Infors) using media as described in Engels et al., The Common Gut Microbe *Eubacterium hallii* also Contributes to Intestinal Propionate Formation, Front. Microbiol., 19 May 2016. The fermentate was concentrated by Cross Flow Filtration in Fermenter A or Fermenter B as described below.

Fermenter A

Cross flow filtration was initiated at pH=7.50 and was performed with a fermentate temperature of 26° C.

Cross flow filtration was slowly started with a feed flow of 300 ml/min. and within approximately 8 minutes the feed rate was gradually increased to 1020 ml/min. At a feed flow of 1020 ml/min., inlet pressure ($P_{in}$) was 0.42 bar(g), TMP was 0.32 bar(g) and permeate flow ($Q_{permeate}$) was 60 ml/min. and the shear rate was 1564 $s^{-1}$. After 20 minutes the back pressure valve was activated with a TMP setpoint of 0.50 bar(g). Corresponding $P_{in}$ was 0.60 bar(g),

| Sample | Damaged | Intermediate cells/ml or cells/g | Intact | Total | Intact % |
|---|---|---|---|---|---|
| Fermenter A | 1.7(±0.03)E+09 | 1.5(±0.03)E+08 | 2.1(±0.03)E+09 | 4.0(±0.01)E+09 | 52.1 |
| Fermenter B | 1.9(±0.07)E+09 | 1.9(±0.03)E+08 | 1.9(±0.05)E+09 | 4.1(±0.11)E+09 | 47.6 |
| Concentrate | 5.6(±0.11)E+10 | 1.4(±0.04)E+10 | 4.0(±0.07)E+10 | 1.1(±0.02)E+11 | 36.2 |
| Pellets (frozen) | 9.5(±1.00)E+10 | 4.7(±0.50)E+09 | 2.7(±0.30)E+09 | 1.0(±0.10)E+11 | 2.7 |
| Freeze dried pellets | 1.1(±0.97)E+11 | 2.7(±2.40)E+09 | 2.4(±3.14)E+08 | 1.1(±0.96)E+11 | 0.15 |
| Milled pellets | 9.1(±9.76)E+10 | 3.9(±4.33)E+09 | 2.5(±3.35)E+08 | 9.2(±9.69)E+10 | 0.17 |
| Electrostatic spray dried | 7.8(±1.70)E+10 | 2.3(±0.50)E+09 | 7.1(±0.50)E+08 | 8.1(±1.70)E+10 | 0.9 |

As it was seen from the flow cytometry results, provided above, there was a high number of total *B. thetaiotaomicron* cells in all the analyzed samples. It was seen that the number of total cells/g through the whole process was quite high and it was seen that the total number of cells/g were in the same range for all the analyzed samples through the full process.

Like the MPN results it was seen that the viability decreased during the freezing step. It was seen that during pelletizing the viability decreased 1.2 log. It was also seen that there was a viability loss during freeze drying of the pellets. The viability of the pellets was decreased 1.0 log during freeze drying.

A decrease in viability was not seen during milling. It was also seen that the number of intact cells of the dried powders; e.g. freeze dried pellets, milled pellets and electrostatic spray dried powder were in the same range. The electrostatic spray dried powder had the highest viability and the viability was 0.5 log higher compared to the freeze dried pellets and the milled pellets.

EXAMPLE 5 PELLETIZING, FREEZE DRYING, MILLING AND ELECTROSTATIC SPRAY DRYING OF *E. HALLII*

The primary objective of this test was to characterize and compare electrostatic spray dried *E. hallii* with pelletized, freeze dried and milled *E. hallii*.

Materials and Methods

Cross flow filtration was carried out identical to Example 3. Two separate fermenters were used. Pelletizing and Freeze Drying were carried out identical to Example 3. Electrostatic spray drying was carried out identical to Example 1.

$Q_{permeate}$=54 ml/min. and shear rate=1581 $s^{-1}$. After approximately 2 hours and 44 minutes, the concentrate was further concentrated by centrifugation.

Fermenter B

Cross flow filtration was initiated at pH=7.30 and was performed with a fermentate temperature of 20° C. Cross flow filtration was slowly started with a feed flow of 800 ml/min. and within approximately 2 minutes the feed rate was gradually increased to 1020 ml/min. At a feed flow of 1020 ml/min., inlet pressure ($P_{in}$) was 0.40 bar(g), TMP was 0.33 bar(g) and permeate flow ($Q_{permeate}$) was 65 ml/min. and the shear rate was 1563 $s^{-1}$. After 24 minutes the back pressure valve was activated with a TMP setpoint of 0.50 bar(g). Corresponding $P_{in}$ was 0.62 bar(g), $Q_{permeate}$=40 ml/min. and shear rate=1604 $s^{-1}$. Following CFF the concentrate had a concentration factor of almost 30×.

The concentrates from fermenter A and B was mixed giving a total concentration factor of 25.12× and with a total solids of concentrate of 8.03% (Mettler Toledo: 105° C.—1 mg/50 s)

Additives, drying protectants, suitable for protecting microorganisms during cryogenic freezing were added to the suspension. These additives (sucrose in the present case) were added such that the ratio between the total solid content of the concentrate and total solid content of these additives were 1:4. TS of concentrate with drying protectant was 25.15% (Mettler Toledo: 60° C.—1 mg/140 s)

Pelletizing and Freeze Drying

A concentrated *E. hallii* fermentate comprising drying protectants was pelletized and freeze dried. Pelletizing was performed without atomization gas and the feed rate was controlled by the Watson Marlow pump, which was set to 2 RPM, which corresponds to approximately 13.86 ml/min. The pelletized material was collected by a 50 µm sieve from Retsch.

The collected pelletized material was transferred to an aluminum bag and kept cold on dry ice until it was transferred to the anaerobic glovebox and thereafter loaded to a freeze drier (Martin Christ). After 46 hours and 10 minutes the freeze drying was ended, and the freeze dried material was removed from the freeze drying tray. The freeze dried material was loaded to a small aluminum bag, which subsequently was sealed by welding.

Properties of the Freeze Dried Pellets

Water activity $(a_w)$=0.024 at 22.89° C.

Residual moisture (RM)=0.44% (Mettler Toledo: 60° C.—1 mg/140 s)

It was not possible to measure particle size distribution on the freeze dried pellets, because they were too big.

Milling of Freeze Dried Pellets:

The milling was performed manually in a mortar for approximately 5 minutes.

Properties of the Milled Pellets:

Water activity $(a_w)$=0.075 at 22.91° C.

Residual moisture (RM)=1.26% (Mettler Toledo: 60° C.—1 mg/140 s)

Mean particle size distribution $(d_{50})$=243 μm

Span=1.985

Electrostatic Spray Drying

During electrostatic spray drying the feed was kept under steering. *E. hallii* concentrate with drying protectant was electrostatic spray dried.

Electrostatic spray drying was performed with a main air flow of 25 m³/h $N_2$. The inlet temperature $(T_{in})$ was 80° C. and the outlet temperature $(T_{out})$ was approximately 36.6° C.

Atomization of the feed was performed with a two-fluid nozzle, where the atomization pressure $(P_{nozzle})$ was 2.0 bar(g) $N_2$ and the atomization temperature was 50° C. The feed rate was controlled by a peristaltic pump with and RPM of 8, which corresponds to approximately 4.8 g/min.

A two-fluid nozzle was used. The electrostatic charge was applied to the suspension, by the use of an electrode in contact with the suspension, located inside the nozzle prior to the nozzle tip where the liquid suspension is atomized into droplets. Pulse Width Modulation (PWM) was used, wherein a 5 kV square pulse, with a pulse length of 1 s, was provided every third second, with a baseline of 1 kV.

During the entire test the oxygen level in the chamber was 0.5% oxygen. The chamber had a vacuum pressure of 0.3 kPa. After the test was ended, dried particles were collected at the outlet end of the drying chamber and analyzed.

Properties of the Electrostatic Spray Dried Product:

Water activity $(a_w)$=0.216 at 22.90° C.

Residual moisture=1.09% (Mettler Toledo: 60° C.—1 mg/140 s)

Mean particle size distribution $(d_{50})$=8.77 μm

Span=4.711

Results

Particle Analytics

For all the produced samples, residual moisture (RM %), water activity $(a_w)$, particle size distribution ($d_{50}$ and span) were measured. In addition, viability was measured for all produced samples by MPN (Most Probable Number) and flow cytometry.

| Sample | $a_w$ | $R_M$ % | $d_{50}$ | Span |
|---|---|---|---|---|
| Pellets | 0.024 | 0.44 | — | — |
| Milled pellets | 0.075 | 1.26 | 243 μm | 1.985 |
| Electrostatic spray dried | 0.216 | 1.09 | 8.77 μm | 4.711 |

From the table above, it can be seen that the water activity was higher for the electrostatic spray dried powder than the pellets and milled pellets. It was also seen that the $a_w$ increased substantially during milling of the pellets. It was not possible to measure the mean particle size of the freeze dried pellets, because the pellets were too large for the Malvern Mastersizer 3000 analytical equipment.

Most Probable Number (MPN):

Growth was measured on the fermentate, concentrate, concentrate+drying protectant, frozen pellets, freeze dried pellets, milled pellets and electrostatic spray dried material.

The cell count pr. ml or cell count pr. gram of all the samples is an average of six analytical results.

| Process step | MPN [pr. mL or pr. g] | Log$_{10}$ MPN | Standard deviation |
|---|---|---|---|
| Fermenter A | 6.2E+08 | 8.8 | 1.3E+08 |
| Fermenter B | 2.0E+07 | 7.3 | 1.3E+07 |
| Concentrate | 1.5E+10 | 10.2 | 1.6E+10 |
| Conc. + drying protectant | 4.6E+09 | 9.7 | 1.2E+09 |
| Frozen pellets | 8.5E+06 | 6.9 | 4.9E+06 |
| Freeze dried pellets | 1.1E+06 | 6.0 | 5.6E+05 |
| Milled pellets | 2.0E+04 | 4.3 | 1.8E+04 |
| Electrostatic spray dried | 1.8E+07 | 7.3 | 6.3E+06 |

From the MPN results it was concluded that the viability decreased by 2.8 log during pelletizing. In addition, the viability decreased 2.6 log during the milling step. The electrostatic spray dried powder had 0.4 log higher viability compared to the freeze dried pellets. The viability of the electrostatic spray dried material was 3.0 log higher compared to the milled pellets.

Flow Cytometry

Flow cytometry was measured on the fermentate, concentrate, concentrate with drying protectant, pelletized material, freeze dried material, milled pellets, and electrostatic spray dried material.

| Sample | Damaged | Intermediate | Intact | Total | Intact % |
|---|---|---|---|---|---|
| | | cells/ml or cells/g | | | |
| Fermenter A | 2.6(±0.3)E+07 | 9.1(±0.3)E+07 | 3.8(±0.0)E+08 | 5.0(±0.05)E+08 | 76.00 |
| Fermenter B | 4.2(±0.0)E+07 | 9.1(±0.0)E+07 | 3.8(±0.04)E+08 | 5.1(±0.04)E+08 | 74.51 |
| Concentrate | 2.9(±0.3)E+08 | 6.0(±0.5)E+08 | 2.0(±0.2)E+09 | 2.9(±0.3)E+09 | 68.97 |
| Pellets (frozen) | 4.3(±0.2)E+08 | 1.0(±0.0)E+09 | 2.8(±0.1)E+07 | 1.5(±0.02)E+09 | 1.87 |
| Freeze dried pellets | 4.0(±0.6)E+09 | 4.5(±0.4)E+08 | 6.1(±1.2)E+07 | 4.4(±0.6)E+09 | 1.39 |
| Milled pellets | 8.9(±0.1)E+09 | 4.5(±0.1)E+08 | 9.7(± 10)E+06 | 9.3(±0.2)E+09 | 0.10 |
| Electrostatic spray dried | 1.8(±0.2)E+09 | 3.2(±0.3)E+09 | 1.8(±0.0)E+07 | 5.0(±0.5)E+09 | 0.36 |

As can be seen from the table above, there was a high number of total *E. hallii* cells in all the analyzed samples. The number of total cells/g in the dried powders were comparable for all the produced powders, with the freeze dried pellets had the highest number of intact cells/g, followed by the electrostatic spray dried powder. There was a viability loss of 0.8 log during the milling of the freeze dried pellets, similar to the MPN analysis. The viability of the electrostatic spray dried powder was 0.8 log lower compared to the freeze dried pellets, but 0.3 log higher compared to the milled pellets.

EXAMPLE 6 PELLETIZING, FREEZE DRYING, MILLING AND ELECTROSTATIC SPRAY DRYING OF *A. MUCINIPHILA*

The primary objective of this test was to characterize and compare electrostatic spray dried *Bacteroides thetaiotaomicron* with pelletized, freeze dried and milled *A. muciniphila*. The characterization of the products included measurements of the respective viabilities of the dried powder from each process.

Materials and Methods

Cross flow filtration was carried out identical to Example 3. Two separate fermenters were used. Pelletizing and Freeze Drying were carried out identical to Example 3.

Electrostatic spray drying was carried out identical to Example 1.

Experimental Work

A culture of *A. muciniphila* was grown in a fermenter (Infors) using media as described in Gómez-Gallego et al., Benef Microbes, 2016 September; 7(4):571-84. The fermentate was concentrated by Cross Flow Filtration in Fermenter A or Fermenter B as described below.

Fermenter A

Cross flow filtration (CFF) was initiated at pH=5.80 and was performed with a fermentate temperature of 37° C. Total solids of the fermentate before concentration were 7.32% (Mettler Toledo: 105° C.—1 mg/50 s). Cross flow filtration was slowly started with a feed flow of 280 ml/min. and within approximately 7 minutes the feed rate was gradually increased to 1680 ml/min. At a feed flow of 1680 ml/min., inlet pressure ($P_{in}$) was 0.17 bar(g), TMP was 0.22 bar(g) and permeate flow ($Q_{permeate}$) was 170 ml/min. and the shear rate was 2480 $s^{-1}$.

After 27 minutes the back pressure valve was activated with a TMP setpoint of 0.30 bar(g). Corresponding $P_{in}$ was 0.26 bar(g), $Q_{permeate}$=165 ml/min. and shear rate=2471 $s^{-1}$. After 1 hour and 2 minutes the TMP setpoint was increased to 0.40 bar(g). Corresponding $P_{in}$ was 0.38 bar(g), $Q_{permeate}$=95 ml/min. and shear rate=2595 $s^{-1}$. A concentration factor of 30× was achieved after approximately 1 hours and 26 minutes.

Fermenter B

Cross flow filtration (CFF) was initiated at pH=5.77 and was performed with a fermentate temperature of 37° C. Cross flow filtration was slowly started with a feed flow of 280 ml/min. and within approximately 7 minutes the feed rate was gradually increased to 1680 ml/min. At a feed flow of 1680 ml/min., inlet pressure ($P_{in}$) was 0.17 bar(g), TMP was 0.22 bar(g) and permeate flow ($Q_{permeate}$) was 160 ml/min. and the shear rate was 2493 $s^{-1}$. After 20 minutes the back pressure valve was activated with a TMP setpoint of 0.30 bar(g). Corresponding $P_{in}$ was 0.25 bar(g), $Q_{permeate}$=150 ml/min. and shear rate=2509 $s^{-1}$. After 56 minutes the TMP setpoint was increased to 0.40 bar(g). Corresponding $P_{in}$ was 0.37 bar(g), $Q_{permeate}$=98 ml/min. and shear rate=2593 $s^{-1}$. A concentration factor of 30× was achieved after approximately 1 hours and 28 minutes.

The collected concentrate from fermenter A and fermenter B was mixed, in total a concentration factor of 30.4× was reached. Total solids of concentrate was 9.85% (Mettler Toledo: 105° C.—1 mg/50 s).

Additives, drying protectants, suitable for protecting microorganisms during cryogenic freezing were added to the suspension. These additives (sucrose in the present case) were added such that the ratio between the total solid content of the concentrate and total solid content of these additives were 1:4. TS of concentrate with drying protectant was 27.85% (Mettler Toledo: 60° C.—1 mg/140 s).

Pelletizing and Freeze Drying

Concentrated *A. muciniphila* fermentate comprising drying protectants was pelletized and freeze dried. Pelletizing was performed without atomization gas and the feed rate was controlled by the Watson Marlow pump, which was set to 2 RPM, which corresponds to approximately 13.86 ml/min. The pelletized material was collected by a 50 μm sieve from Retsch.

The collected pelletized material was transferred to an aluminum bag and kept cold on dry ice until it was transferred to the anaerobic glovebox and thereafter loaded to a freeze drier (Martin Christ). After 46 hours and 10 minutes the freeze drying was ended, and the freeze dried material was removed from the freeze drying tray.

The freeze dried material was loaded to a small aluminum bag, which subsequently was sealed by welding.

Properties of the Freeze Dried Pellets

Water activity ($a_w$)=0.089

Residual moisture=0.25% (Mettler Toledo: 60° C.—1 mg/140 s)

It was not possible to measure particle size distribution on the freeze dried pellets, because they were too big.

Milling of Freeze Dried Pellets

The milling was performed manually in a mortar for approximately 5 minutes.

Properties of the Milled Pellets

Water activity ($a_w$)=0.206

Residual moisture=1.25% (Mettler Toledo: 60° C.—1 mg/140 s)

Mean particle size distribution ($d_{50}$)=808 μm

Span=2.633

Electrostatic Spray Drying

*A. muciniphila* concentrate with drying protectant was electrostatic spray dried, during electrostatic spray drying the feed was kept under steering.

Electrostatic spray drying was performed with a main air flow of 25 $m^3$/h N2.

The inlet temperature ($T_{in}$) was 80° C. and the outlet temperature ($T_{out}$) was approximately 38.5° C. Atomization of the feed was performed with a two-fluid nozzle, where the atomization pressure ($P_{nozzle}$) was 2.0 bar(g) N2 and the atomization temperature was 50° C. The feed rate was controlled by a peristaltic pump with and RPM of 6, which corresponds to approximately 3.5 g/min.

A two-fluid nozzle was used. The electrostatic charge was applied to the suspension, by the use of an electrode in contact with the suspension, located inside the nozzle prior to the nozzle tip where the liquid suspension is atomized into droplets. Pulse Width Modulation (PWM) was used, wherein a 5 kV square pulse, with a pulse length of 1 s, was provided every third second, with a baseline of 1 kV.

After the test was ended, dried particles were collected at the outlet end of the drying chamber and analyzed.

Properties of the Electrostatic Spray Dried Product:

Water activity ($a_w$)=0.167

Residual moisture ($R_m$%)=2.01% (Mettler Toledo: 60° C.—1 mg/140 s)

Mean particle size distribution ($d_{50}$)=6.63 μm

Span=4.693 and the viability was 0.5 log higher compared to the powder produced by freeze drying of pellets.

Flow Cytometry

Flow cytometry was measured on the fermentate, concentrate, concentrate with drying protectant, pelletized material, freeze dried pellets, milled pellets and electrostatic spray dried material.

| Sample | Damaged | Intermediate cells/ml or cells/g | Intact | Total | Intact % |
|---|---|---|---|---|---|
| Fermenter A | 3.9(±1.2)E+07 | 2.9(±0.2)E+08 | 7.0(±0.1)E+09 | 7.3(±0.1)E+09 | 95.4 |
| Fermenter B | 7.8(±1.5E+07 | 1.3(±0.06)E+08 | 4.1(±0.2)E+09 | 4.3(±0.2)E+09 | 95.2 |
| Concentrate | 1.3(±0.2)E+09 | 6.8(±0.5)E+09 | 1.3(±0.2)E+11 | 1.4(±0.2)E+11 | 94.3 |
| Pellets (frozen) | 1.0(±0.2)E+09 | 9.8(±0.6)E+09 | 1.1(±0.1)E+11 | 1.2(±0.1)E+11 | 90.9 |
| Freeze dried pellets | 2.3(±0.4)E+09 | 2.5(±0.4)E+10 | 1.4(±0.1)E+11 | 1.7(±0.1)E+11 | 84.2 |
| Milled pellets | 2.5(±0.1)E+09 | 2.7(±0.1)E+10 | 1.6(±0.05)E+11 | 1.9(±0.06)E+11 | 84.7 |
| Electrostatic spray dried | 3.5(±0.5)E+09 | 8.3(±1.7)E+09 | 2.4(±0.1)E+11 | 2.5(±0.1)E+11 | 95.3 |

Results

Particle Analytics

For all the produced samples, residual moisture ($R_M$%), water activity ($a_w$), particle size distribution ($d_{50}$ and span) was measured. Viability was also measured for all produced samples, by MPN (Most Probable Number) and flow cytometry.

| Sample | $a_w$ | $R_M$% | $d_{50}$ | Span |
|---|---|---|---|---|
| Pellets | 0.089 | 0.25 | — | — |
| Milled pellets | 0.206 | 1.25 | 808 μm | 2.633 |
| Electrostatic spray dried | 0.167 | 2.01 | 6.63 μm | 4.693 |

The table above shows that the water activity increased significantly during milling of the pellets. It was not possible to measure the mean particle size of the freeze dried pellets, because the pellets were too large for the Malvern Mastersizer 3000 analytical equipment.

Most Probable Number (MPN):

Growth was measured on the fermentate, concentrate, concentrate+drying protectant, frozen pellets, freeze dried pellets, milled pellets and electrostatic spray dried material. The cell count pr. ml or cell count pr. gram of all the samples is an average of six analytical results.

| Process step | MPN [pr. mL or pr. g] | Log10 MPN | Standard deviation |
|---|---|---|---|
| Fermenter A | 6.5E+08 | 8.8 | 1.7E+08 |
| Fermenter B | 2.9E+08 | 8.5 | 0.0E+00 |
| Concentrate | 8.2E+09 | 9.9 | 4.0E+09 |
| Conc. + drying protectant | 1.0E+10 | 10.0 | 4.2E+09 |
| Frozen pellets | 4.2E+10 | 10.6 | 1.4E+09 |
| Freeze dried pellets | 3.1E+10 | 10.5 | 6.9E+09 |
| Milled pellets | 7.5E+10 | 10.9 | 3.0E+10 |
| Electrostatic spray dried | 9.6E+10 | 11.0 | 5.1E+10 |

From the MPN results in the table above, it can be seen that a high viability was achieved and that there was no viability loss during the freezing step. The viability of the dried powders; e.g. freeze dried pellets, milled pellets and electrostatic spray dried powder were in the same range. Electrostatic spray dried powder had the highest viability As can be seen from the flow cytometry results, provided in the table above, there was a high number of intact *A. muciniphila* cells in all the analyzed samples. The number of total cells/g in the dried powders were quite high and they were comparable for all the produced powders, similar to the MPN analysis.

As in the MPN analysis it was seen that the number of intact cells of the dried powders; e.g. freeze dried pellets, milled pellets and electrostatic spray dried powder were in the same range. Electrostatic spray dried powder had the highest viability and the viability was 0.3 log higher compared to the powder produced from freeze drying of pellets.

The invention claimed is:

1. A process for electrostatic spray drying of a living microorganism, the process comprising:

applying an electrostatic charge to a suspension comprising a live microorganism, a solvent, and an additive, wherein the suspension comprises at least 35% by weight water;

forming droplets of said suspension;

drying said droplets, thereby forming dried particles; and collecting the dried particles;

wherein the solvent has a higher dielectric constant than the additive, and the additive has a higher dielectric constant than the microorganism.

2. The process according to claim 1, wherein the electrostatic charge is applied by an electrode in contact with said suspension, wherein said electrode has an electric potential difference, with respect to ground, below about 40 kV.

3. The process according to claim 2, wherein the electric potential difference, with respect to ground, of the electrode varies over time.

4. The process according to claim 1, wherein the microorganism comprises facultative anaerobic bacteria or strict anaerobic bacteria.

5. The process according to claim 1, wherein forming droplets is carried with a two-fluid nozzle.

6. The process according to claim 1, wherein forming droplets is carried out with an atomizing gas selected from one or more of an inert gas, a noble gas, and an alkane gas.

7. The process according to claim 1, wherein the suspension comprises as at least 40% by weight water.

8. The process according to claim 1, wherein the additive comprises a drying protectant.

9. The process according to claim 8, wherein the dried particle comprises the drying protectant in an amount from about 50% by weight to about 90% by weight.

10. The process according to claim 8, wherein the additive comprises a drying protectant comprising one or more selected from cyclitols, monosaccharides, disaccharides, polysaccharides, magnesium stearate, peptides, proteins, sugar alcohols, hydrogenated starch hydrolysates, fatty acid esters, and alginates and salts thereof.

11. The process according to claim 8, wherein the additive comprises a drying protectant comprising one or more selected from inositol, dextrose, lactose, sucrose, trehalose, inulin, maltodextrin, starch, magnesium stearate, mannitol, sorbitol, and sodium alginate.

12. The process according to claim 8, wherein the dried particle comprises the drying protectant in an amount from about 50% by weight to about 75% by weight.

13. The process according to claim 1, wherein the dried particles have a size from about 10 micrometers to about 200 micrometers, measured as Dv50 values.

14. The process according to claim 1, wherein the size distribution of the dried particles is substantially unimodal.

15. The process according to claim 1, wherein the dried particles comprise a microorganism having a viability of at least 1.0×10E4 per gram, as determined by one or more of the most probable number (MPN), the number of colony forming units (CFU), and the number of viable cells as measured by flow cytometry.

16. The process according to claim 1, wherein the electrostatic charge is applied by an electrode in contact with said suspension, wherein said electrode has an electric potential difference, with respect to ground, below about 25 kV.

17. The process according to claim 1, wherein the electrostatic charge is applied by an electrode in contact with said suspension, wherein said electrode has an electric potential difference, with respect to ground, below about 10 kV.

18. The process according to claim 1, wherein the suspension comprises at least 50% by weight water.

19. The process according to claim 1, wherein the suspension comprises at least 70% by weight water.

20. The process according to claim 1, wherein the dried particles have a size from about 50 micrometers to about 200 micrometers, measured as Dv50 values.

21. The process according to claim 1, wherein the dried particles have a size from about 100 micrometers to about 200 micrometers, measured as Dv50 values.

\* \* \* \* \*